(12) United States Patent
Hodgetts et al.

(10) Patent No.: US 9,237,992 B2
(45) Date of Patent: Jan. 19, 2016

(54) TWO-STEP MASCARA PRODUCT

(75) Inventors: Jennifer Clare Hodgetts, Maidenhead (GB); Angela Michele Fabula, Baldwin, MD (US); Thomas Elliott Rabe, Baltimore, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/457,252

(22) Filed: Apr. 26, 2012

(65) Prior Publication Data

US 2012/0298128 A1    Nov. 29, 2012

Related U.S. Application Data

(63) Continuation-in-part of application No. 13/274,852, filed on Oct. 17, 2011, and a continuation-in-part of application No. 12/912,478, filed on Oct. 26, 2010.

(60) Provisional application No. 61/455,843, filed on Oct. 27, 2010, provisional application No. 61/255,457, filed on Oct. 27, 2009.

(51) Int. Cl.
*A61K 8/02* (2006.01)
*A61K 8/19* (2006.01)
(Continued)

(52) U.S. Cl.
CPC ............... *A61K 8/19* (2013.01); *A61K 8/0241* (2013.01); *A61K 8/26* (2013.01); *A61K 8/31* (2013.01); *A61K 8/375* (2013.01); *A61K 8/922* (2013.01); *A61K 8/927* (2013.01); *A61Q 1/10* (2013.01); *A61K 2800/412* (2013.01); *A61K 2800/622* (2013.01); *A61K 2800/624* (2013.01); *A61K 2800/87* (2013.01); *A61K 2800/88* (2013.01)

(58) Field of Classification Search
CPC ........................................................ A61Q 1/10
See application file for complete search history.

(56) References Cited

U.S. PATENT DOCUMENTS 2,458,063 A    1/1949    Duhlberg
2,831,854 A    4/1958    Tucker
(Continued)

FOREIGN PATENT DOCUMENTS

CN    300856708    12/2008
CN    300856709    12/2008
(Continued)

OTHER PUBLICATIONS

PCT International Search Report and Written Opinion for PCT/US2013/038339 dated Sep. 12, 2013.
(Continued)

*Primary Examiner* — Hasan Ahmed
(74) *Attorney, Agent, or Firm* — Betty J. Zea

(57) ABSTRACT

A two-step mascara product that includes a first mascara composition and a second mascara composition. The first mascara composition includes a film-forming polymer dispersed in a first carrier, and the second mascara composition includes a film-former selected from the group consisting of tall oil glycerides, pentaerythrityl rosinate, glyceryl rosinate, hydrogenated versions of these and mixtures thereof. The two-step mascara product also includes a package for storing and dispensing each of the first and second mascara compositions. The package includes a first container configured to store and dispense the first mascara composition and a second container configured to store and dispense the second composition.

1 Claim, 14 Drawing Sheets

(51) Int. Cl.
*A61K 8/26* (2006.01)
*A61K 8/92* (2006.01)
*A61Q 1/10* (2006.01)
*A61K 8/31* (2006.01)
*A61K 8/37* (2006.01)

(56) References Cited

U.S. PATENT DOCUMENTS

| | | |
|---|---|---|
| 2,900,306 A | 8/1959 | Slater |
| 3,255,082 A | 6/1966 | Barton |
| 3,677,271 A | 7/1972 | Luciano |
| 3,690,777 A | 9/1972 | Costa |
| 3,739,789 A | 6/1973 | Cataneo |
| 3,802,841 A | 4/1974 | Robin |
| 3,963,699 A | 6/1976 | Rizzi et al. |
| 4,005,195 A | 1/1977 | Jandacek |
| 4,005,196 A | 1/1977 | Jandacek et al. |
| 4,126,679 A | 11/1978 | Davy et al. |
| 4,137,306 A | 1/1979 | Rubino et al. |
| 4,151,272 A | 4/1979 | Geary et al. |
| 4,154,816 A | 5/1979 | Roehl et al. |
| D252,911 S | 9/1979 | Levy |
| 4,202,879 A | 5/1980 | Shelton |
| 4,226,889 A | 10/1980 | Yuhas |
| 4,228,277 A | 10/1980 | Landoll |
| 4,229,432 A | 10/1980 | Geria |
| 4,280,994 A | 7/1981 | Turney |
| 4,322,400 A | 3/1982 | Yuhas |
| 4,336,246 A | 6/1982 | Leon-Pekarek |
| 4,346,079 A | 8/1982 | Roehl |
| 4,383,988 A | 5/1983 | Teng et al. |
| D277,324 S | 1/1985 | Davey |
| 4,517,360 A | 5/1985 | Volpenhein |
| 4,518,772 A | 5/1985 | Volpenhein |
| 4,725,432 A | 2/1988 | May |
| 4,759,924 A | 7/1988 | Luebbe et al. |
| 4,797,300 A | 1/1989 | Jandacek et al. |
| 4,816,261 A | 3/1989 | Luebbe et al. |
| 4,886,080 A | 12/1989 | Cole |
| 4,932,802 A | 6/1990 | Cantone |
| 4,980,155 A | 12/1990 | Shah et al. |
| 5,017,398 A | 5/1991 | Jandacek et al. |
| 5,019,375 A | 5/1991 | Tanner et al. |
| 5,040,914 A | 8/1991 | Fitjer |
| 5,097,853 A | 3/1992 | Nehashi |
| 5,104,646 A | 4/1992 | Bolich, Jr. et al. |
| RE33,996 E | 7/1992 | Jandacek |
| 5,165,917 A | 11/1992 | Zabotto |
| 5,193,918 A | 3/1993 | Lohrmann et al. |
| 5,306,514 A | 4/1994 | Letton et al. |
| 5,306,515 A | 4/1994 | Letton et al. |
| 5,306,516 A | 4/1994 | Letton et al. |
| RE34,617 E | 5/1994 | Jandacek et al. |
| 5,376,231 A | 12/1994 | Matsumoto et al. |
| 5,389,363 A | 2/1995 | Snyder |
| D360,486 S | 7/1995 | Schultz |
| 5,490,529 A * | 2/1996 | Fitjer ............................ 132/218 |
| 5,794,632 A | 8/1998 | Gueret |
| 5,832,942 A | 11/1998 | Gutberlet |
| 5,843,417 A * | 12/1998 | Hanna et al. ................. 424/70.7 |
| 5,866,434 A | 2/1999 | Massey et al. |
| D422,748 S | 4/2000 | Lang |
| 6,071,503 A | 6/2000 | Drechsler et al. |
| 6,074,654 A | 6/2000 | Drechsler et al. |
| 6,080,687 A | 6/2000 | Ishwarlal |
| 6,139,823 A | 10/2000 | Drechsler et al. |
| 6,200,045 B1 | 3/2001 | Hahn et al. |
| 6,203,814 B1 | 3/2001 | Fisher et al. |
| 6,241,408 B1 | 6/2001 | Lang |
| 6,267,951 B1 | 7/2001 | Shah et al. |
| 6,303,105 B1 | 10/2001 | Shah et al. |
| D450,888 S | 11/2001 | Breidenbach et al. |
| 6,340,466 B1 | 1/2002 | Drechsler et al. |
| D453,588 S | 2/2002 | Breidenbach et al. |
| D453,589 S | 2/2002 | Breidenbach et al. |
| 6,450,179 B2 | 9/2002 | Bengis |
| 6,464,418 B1 | 10/2002 | Visser |
| 6,488,427 B1 | 12/2002 | Breidenbach et al. |
| 6,491,902 B2 | 12/2002 | Shefer et al. |
| 6,500,446 B1 | 12/2002 | Derrieu et al. |
| D474,341 S | 5/2003 | Cantone et al. |
| 6,612,764 B2 | 9/2003 | Dumler |
| 6,637,963 B2 | 10/2003 | Huang |
| D482,284 S | 11/2003 | Cantone et al. |
| 6,682,242 B1 | 1/2004 | Montoli |
| D497,455 S | 10/2004 | Lee |
| 6,811,770 B2 | 11/2004 | Ferrari et al. |
| 6,979,440 B2 | 12/2005 | Shefer et al. |
| 6,985,879 B2 | 1/2006 | Walker et al. |
| 7,077,591 B2 | 7/2006 | Gueret |
| D530,857 S | 10/2006 | Black |
| 7,168,875 B1 | 1/2007 | Zhang |
| 7,175,359 B2 | 2/2007 | Zhang |
| 7,186,274 B2 | 3/2007 | Vic et al. |
| D542,978 S | 5/2007 | Bortolotti |
| 7,210,870 B2 | 5/2007 | Breidenbach et al. |
| 7,226,227 B2 | 6/2007 | Gueret |
| 7,241,835 B2 | 7/2007 | O'Brien et al. |
| 7,276,088 B2 | 10/2007 | Huang et al. |
| D561,390 S | 2/2008 | Sugawara |
| D566,335 S | 4/2008 | Althoff et al. |
| D566,337 S | 4/2008 | Althoff et al. |
| D574,154 S | 8/2008 | Dumler et al. |
| D574,155 S | 8/2008 | Dumler et al. |
| D578,770 S | 10/2008 | Berhault |
| D579,208 S | 10/2008 | Berhault |
| 7,438,953 B2 | 10/2008 | Kotov et al. |
| D581,169 S | 11/2008 | Berhault |
| D583,506 S | 12/2008 | Justice |
| D585,600 S | 1/2009 | Althoff et al. |
| 7,473,045 B2 * | 1/2009 | Dumler ............................ 401/17 |
| D592,858 S | 5/2009 | Berhault |
| D593,330 S | 6/2009 | Berhault |
| D593,331 S | 6/2009 | Berhault |
| D598,657 S | 8/2009 | Berhault |
| D600,921 S | 9/2009 | Berhault |
| D600,922 S | 9/2009 | Berhault |
| D600,923 S | 9/2009 | Berhault |
| 7,632,489 B2 | 12/2009 | Wyatt et al. |
| D615,419 S | 5/2010 | Owen |
| 7,780,875 B2 | 8/2010 | Asgari |
| 7,842,285 B2 | 11/2010 | Lu et al. |
| 7,856,806 B1 | 12/2010 | Chasman et al. |
| D634,127 S | 3/2011 | Burgess et al. |
| D634,478 S | 3/2011 | Kolas et al. |
| D636,940 S | 4/2011 | Acierto et al. |
| D642,805 S | 8/2011 | Burgess et al. |
| 7,993,661 B2 | 8/2011 | Arnaud et al. |
| D653,398 S | 1/2012 | Acierto et al. |
| 8,096,306 B2 | 1/2012 | Malvar et al. |
| D654,626 S | 2/2012 | Kolas et al. |
| 8,168,095 B2 | 5/2012 | Alberius et al. |
| 8,298,494 B2 | 10/2012 | Komiya et al. |
| 8,323,628 B2 | 12/2012 | Atis |
| 8,329,147 B2 | 12/2012 | Ansmann et al. |
| 8,336,560 B2 | 12/2012 | Dumler et al. |
| 8,444,930 B2 | 5/2013 | Komiya et al. |
| 2001/0051168 A1 | 12/2001 | Ramin et al. |
| 2002/0071707 A1 | 6/2002 | Breidenbach et al. |
| 2002/0076390 A1 | 6/2002 | Kantner et al. |
| 2002/0083954 A1 | 7/2002 | Gavney |
| 2002/0185148 A1 | 12/2002 | Bengis |
| 2002/0190336 A1 | 12/2002 | Shimizu et al. |
| 2003/0031642 A1 * | 2/2003 | Lezer ............................ 424/70.12 |
| 2003/0041870 A1 | 3/2003 | Su |
| 2003/0086741 A1 | 5/2003 | Kim |
| 2003/0095935 A1 | 5/2003 | Chaiyawat et al. |
| 2003/0143181 A1 | 7/2003 | Hensen et al. |
| 2004/0105828 A1 | 6/2004 | Chaiyawat et al. |
| 2004/0115232 A1 | 6/2004 | Giroud et al. |
| 2004/0126303 A1 | 7/2004 | Hwang |
| 2004/0190974 A1 | 9/2004 | Cantone et al. |
| 2004/0228890 A1 | 11/2004 | Blin et al. |
| 2004/0234564 A1 | 11/2004 | Blin et al. |

(56) References Cited

U.S. PATENT DOCUMENTS

| | | |
|---|---|---|
| 2005/0095213 A1 | 5/2005 | Blin et al. |
| 2005/0176598 A1 | 8/2005 | Bergquist et al. |
| 2005/0186167 A1 | 8/2005 | Ueda et al. |
| 2005/0276779 A1 | 12/2005 | Blin |
| 2006/0029560 A1 | 2/2006 | Blin |
| 2006/0067783 A1 | 3/2006 | Tsaur |
| 2006/0127339 A1 | 6/2006 | Bavouzet et al. |
| 2006/0134035 A1 | 6/2006 | Zheng et al. |
| 2006/0189554 A1 | 8/2006 | Mumper et al. |
| 2006/0260633 A1 | 11/2006 | Wyatt et al. |
| 2006/0275232 A1 | 12/2006 | Chevalier |
| 2007/0020205 A1* | 1/2007 | Blin et al. ............... 424/61 |
| 2007/0041920 A1 | 2/2007 | Blin et al. |
| 2007/0048238 A1 | 3/2007 | Sandewicz et al. |
| 2007/0140991 A1 | 6/2007 | Maitra et al. |
| 2007/0274941 A9 | 11/2007 | Blin |
| 2007/0286824 A1 | 12/2007 | Rabe et al. |
| 2008/0000491 A1 | 1/2008 | Bodelin |
| 2008/0014232 A1 | 1/2008 | Arnaud et al. |
| 2008/0056807 A1 | 3/2008 | Vintimiglia |
| 2008/0107615 A1 | 5/2008 | Keene et al. |
| 2008/0115798 A1 | 5/2008 | Rainey et al. |
| 2008/0124350 A1 | 5/2008 | Mumper et al. |
| 2008/0171009 A1 | 7/2008 | Auguste et al. |
| 2008/0226575 A1 | 9/2008 | Hanna |
| 2008/0311063 A1 | 12/2008 | Shah et al. |
| 2009/0010868 A1 | 1/2009 | Ilekti et al. |
| 2009/0098170 A1 | 4/2009 | D'Acchioli et al. |
| 2009/0142282 A1 | 6/2009 | Kendall et al. |
| 2009/0193602 A1* | 8/2009 | Dumler et al. ............... 15/160 |
| 2009/0193692 A1 | 8/2009 | Lipczynski |
| 2009/0263658 A1 | 10/2009 | Alberius et al. |
| 2009/0317350 A1 | 12/2009 | Lu et al. |
| 2010/0003205 A1 | 1/2010 | Elliott et al. |
| 2010/0003293 A1 | 1/2010 | Elliott et al. |
| 2010/0028612 A1 | 2/2010 | Gruber et al. |
| 2010/0068163 A1* | 3/2010 | Lu ............... 424/70.7 |
| 2010/0074928 A1 | 3/2010 | Elliott et al. |
| 2010/0152135 A1 | 6/2010 | Blin |
| 2010/0179105 A1 | 7/2010 | Blin et al. |
| 2011/0094533 A1 | 4/2011 | Dempsey et al. |
| 2011/0094914 A1 | 4/2011 | Dempsey et al. |
| 2011/0117040 A1 | 5/2011 | Dempsey et al. |
| 2011/0117043 A1 | 5/2011 | Dempsey et al. |
| 2011/0268490 A1 | 11/2011 | Acierto et al. |
| 2012/0114585 A1 | 5/2012 | Dempsey et al. |
| 2012/0269753 A1 | 10/2012 | Rabe et al. |
| 2012/0298128 A1 | 11/2012 | Hodgetts et al. |
| 2012/0315076 A1 | 12/2012 | Bekele et al. |
| 2013/0012594 A1 | 1/2013 | Hirasawa et al. |
| 2013/0056016 A1 | 3/2013 | Guay et al. |
| 2013/0056019 A1 | 3/2013 | Wilson et al. |
| 2013/0056020 A1 | 3/2013 | Wilson et al. |

FOREIGN PATENT DOCUMENTS

| | | |
|---|---|---|
| CN | 300856710 | 12/2008 |
| CN | 102360416 A | 2/2012 |
| DE | 3923731 A1 | 1/1991 |
| EM | 000345483.003 | 7/2005 |
| EM | 000386388.0001 | 11/2005 |
| EM | 000386388.0002 | 11/2005 |
| EM | 000386388.0020 | 11/2005 |
| EM | 000386388.0028 | 11/2005 |
| EM | 000386388.0030 | 11/2005 |
| EM | 000386388.0031 | 11/2005 |
| EM | 000386388.0034 | 11/2005 |
| EM | 000500418.001 | 5/2006 |
| EM | 000540869.0021 | 7/2006 |
| EM | 000540869.0024 | 7/2006 |
| EM | 000603808.002 | 11/2006 |
| EM | 000623202.0002 | 12/2006 |
| EM | 000623202.0004 | 12/2006 |
| EM | 000623202.0009 | 12/2006 |
| EM | 000623202.0010 | 12/2006 |
| EM | 000623202.0011 | 12/2006 |
| EM | 000623202.0012 | 12/2006 |
| EM | 000623202.0013 | 12/2006 |
| EM | 000614706.001 | 1/2007 |
| EM | 000654272.0003 | 4/2007 |
| EM | 000654272.0004 | 4/2007 |
| EM | 000654272.0005 | 4/2007 |
| EM | 000688007.0002 | 4/2007 |
| EM | 000688007.0003 | 4/2007 |
| EM | 000871017.0001 | 2/2008 |
| EM | 000871017.0007 | 2/2008 |
| EM | 000871017.0008 | 2/2008 |
| EM | 000871017.0009 | 2/2008 |
| EM | 000871017.0010 | 2/2008 |
| EM | 000871017.0014 | 2/2008 |
| EM | 000871017.0015 | 2/2008 |
| EM | 000871017.0016 | 2/2008 |
| EM | 000871017.0024 | 2/2008 |
| EM | 000871017.0025 | 2/2008 |
| EM | 000871017.0026 | 2/2008 |
| EM | 000871017.0027 | 2/2008 |
| EM | 000871017.0028 | 2/2008 |
| EM | 000871017.0029 | 2/2008 |
| EM | 000871017.0030 | 2/2008 |
| EM | 000871017.0031 | 2/2008 |
| EM | 000871017.0032 | 2/2008 |
| EM | 000871017.0033 | 2/2008 |
| EM | 000871017.0037 | 2/2008 |
| EM | 000871017.0038 | 2/2008 |
| EM | 000871017.0039 | 2/2008 |
| EM | 000871017.0040 | 2/2008 |
| EM | 000871017.0043 | 2/2008 |
| EM | 000871017.0044 | 2/2008 |
| EM | 000871017.0054 | 2/2008 |
| EM | 000871017.0055 | 2/2008 |
| EM | 000871017.0056 | 2/2008 |
| EM | 000871017.0057 | 2/2008 |
| EM | 000871017.0058 | 2/2008 |
| EM | 000871017.0059 | 2/2008 |
| EM | 000871017.0060 | 2/2008 |
| EM | 000871017.0061 | 2/2008 |
| EP | 0024365 B1 | 3/1981 |
| EP | 549494 | 6/1993 |
| EP | 1238603 A3 | 9/2003 |
| FR | 2079785 | 10/1971 |
| FR | 000975286.0001 | 12/1997 |
| FR | 2898469 A1 | 9/2007 |
| FR | 2919477 A1 | 2/2009 |
| GB | 2124081 A | 2/1984 |
| GB | 2293545 A | 4/1996 |
| JP | 03173811 | 7/1991 |
| JP | 2004168169 A | 7/2004 |
| JP | 200423863 | 8/2004 |
| JP | 2004339212 A | 12/2004 |
| JP | 2006174936 A | 7/2006 |
| JP | 2006282585 | 10/2006 |
| JP | 0D1207926 | 5/2007 |
| JP | 2009114099 | 5/2009 |
| JP | 2009137841 | 6/2009 |
| KR | 300424071.0001 | 2/2006 |
| KR | 300465977.0000 | 10/2007 |
| KR | 300488446.0000 | 4/2008 |
| KR | 300507379.0000 | 9/2008 |
| WO | 000011033.003 | 7/1988 |
| WO | 000014434.0010 | 10/1989 |
| WO | 000014434.0011 | 10/1989 |
| WO | 000014434.0025 | 10/1989 |
| WO | 96/20698 | 7/1996 |
| WO | 000042185.0001 | 2/1998 |
| WO | 000042185.0002 | 2/1998 |
| WO | 000042185.0003 | 2/1998 |
| WO | 000042185.0004 | 2/1998 |
| WO | 00/47177 | 8/2000 |
| WO | 000054973.0006 | 3/2001 |
| WO | 01/45652 | 6/2001 |
| WO | 2004073662 A1 | 9/2004 |
| WO | 2006/058795 | 6/2006 |
| WO | 2006/078541 | 7/2006 |

(56) References Cited

FOREIGN PATENT DOCUMENTS

| WO | WO2007/040517 | * | 4/2007 | ............... A61Q 1/10 |
| WO | 2008/074870 A2 | | 6/2008 | |
| WO | 2008089926 A | | 7/2008 | |
| WO | 2012/011043 A1 | | 1/2012 | |

OTHER PUBLICATIONS

R. Pigeon and P. Allard, Chimie Macromo-culaire Applique, 40141 (1974), pp. 139-158 (No. 600).
PCT International Search Report and Written Opinion for PCT/US2012/038231 dated Aug. 21, 2012.
Avon, Avon Colour, In a Blink Eye Shadow and Liner, date published Mar. 2007; www.gnpd.com, 2 pages.
Avon, Avon, Blueberry Cool/Black Lush Lips and Long Lashes, date published Mar. 2006; www.gnpd.com, 2 pages.
Avon, Avon, Dual Ended Eye-Liner, date published Oct. 2007; www.gnpd.com, 2 pages.
Avon, Avon, Shimmer Shadow and Liner, date published Jun. 2007; www.gnpd.com, 2 pages.
Avon, MistakeProof Mascara, date published Oct. 2008; www.gnpd.com, 4pages.
Bare Escentuals, bareMinerals Tutorials, Lesson 1: Get Cheeky, date published Feb. 2008; www.gnpd.com, 1 page.
Bare Escentuals, bareMinerals, Get Started: Eyes, Cheeks, Lips Set, date published Mar. 2008; www.gnpd.com, 1 page.
Bobbi Brown Copper Diamond, Everything/Lash Glamour Mascara Duo, date published Nov. 2008; www.gnpd.com, 3 pages.
Bobbi Brown, Bobbi Brown Christmas 2008, Night Sky Long-Wear Eye Palette, date published Dec. 2008; www.gnpd.com, 3 pages.
Bobbi Brown, Honey Glaze Long-Wear Eye Palette, date published Apr. 2009; www.gnpd.com, 3 pages.
Bobbi Brown, Lip and Eye Basics Palette, date published Sep. 2006; www.gnpd.com, 2 pages.
Bobbi Brown, Shimmering Nudes Collection, Shimmering Nudes Palette, date published Oct. 2008; www.gnpd.com, 3 pages.
Caboodles Color Tips, Mascara Extension, date published Dec. 2005; www.gnpd.com, 2 pages.
Cosmetobelleza Natural IM, Double Effect Mascara, date published: Jul. 2009; www.gnpd.com, 2 pages.
Creative Brands, Australis, Eyeshadow, date published Aug. 2007; www.gnpd.com, 2 pages.
Del Laboratories, Sally Hensen Healing Beauty, Thicken-Up Plumper + Mascara, date published Oct. 2003; www.gnpd.com, 2 pages.
Gurwitch Products, Laura Mercier, Limited-Edition Eye Book, date published Dec. 2008; www.gnpd.com, 2 pages.
Gurwitch Products, Laura Mercier, Beauty Library Set, date published Dec. 2006; www.gnpd.com, 3 pages.
Helena Rubinstein, Surrealist Mascara & Liner, date pubiished Nov. 2006; www.gnpd.com, 2 pages.
Invima, Isadora Wonder Full Mascara, date published Sep. 2006; www.gnpd.com, 2 pages.
Kao, Aube Couture, Desgning Double Mascara, date oublished Dec. 2008, www.gnpd.com, 3 pages.
Isehan, Kiss Me Mascara Remover, date pubbshed Sep. 2008; www.gnpd.com, 2 pages.
Kose, Fasio Easy Mascara Remover, date published Jun. 2009; www-w.gnpd.com, 3 pages.
Kose, Fasio Mascara Easy Remover, date published Jan. 2009; www-w.gnpd.com, 2 pages.
Lorac Cosmetics, Lorac, Fairytale Life Makeup Collection, date published Dec. 2007; www.gnpd.com; 4 pages.
L'Oréal Double Mascara, Date published May 2006; www.gnpd.com, 2 pages.
Maqullage Shisiedo, Mascara Remover, date published Jun. 2008; wwww.gnpd.com, 2 pages.
Napoleon Perdis Cosmetics, NP Set Eyeliner, date published Mar. 2009; www.gnpd.com, 4 pages.
Napoleon Perdis Cosmetics, NP Set Eye Palette, date published Feb. 2009 www.gnpd.com, 3 pages.
Prestige Cosmetics, Glitter Lash Mascara, date published Dec. 2008, www.gnpd.com, 2 pages.
Revlon, Limited Edition Dual Lesh Mystique Mascara, date published Jun. 2003; www.gnpd.com, 1 page.
Rimmel , Coty, Volume Extend Waterproof Mascara, date published Sep. 2006; www.gnpd.com, 2 pages.
Rimmel, Double Play Multi Look Mascara, date published Apr. 2007; Mar. 2007; www.gnpd.com, 2 pages.
Rossman, Rival de Loop Young, Double Brush Mascara, date published: Oct. 2009; www.gnpd.com, 2 pages.
Shiseldo, The Makeup Eraser Pencil, date published Jun. 2001; wwww.gnpd.com, 2 pages.
Sleek Makeup, Duo Dip It Mascara + Eyeliner, date published Mar. 27, 2009; www.gnpd.com, 3 pages.
SmashBox Limitless Lash Mascara, date published May 2003 www.gnpd.com, 2 pages.
Swab Plus Eye Makeup Remover Swabs , date published Nov. 2007; wwww.gnpd.com, 2 pages.
SwabPlus Waterproof Mascara Remover Swabs, date published Dec. 2002; wwww.gnpd.com, 2 pages.
Tarte Cosmetics, Tarte Fall 2008, Eye Couture Day-to-Night Eye Palette, date published Aug. 2008; www.gnpd.com, 2 pages.
The Art of Makeup, VIP Complete Cosmetic Kit, date published Feb. 2008; www.gnpd.com 4 pages.
Narus Cosmetics, Wink Up Mascara Remover, date published Mar. 1999; www.gnpd.com, 1 page.
Xtreme Color, Mary-Kate and Ashley, Eye Drama Creme Eye Color Plus Rich Mascara, date published Jul. 2004; wwww.gnpd.com, 2 pages.
Yves Saint Laurent; Yves Saint Laurent Parfums; Duo Expert Sourcils, date published Nov. 2004; www.gnpd.com, 1 page.
PCT International Search Report and Written Opinion for PCT/US2013/041135 dated Nov. 8, 2013.
PCT International Search Report and Written Opinion for PCT/US2010/054090 dated Feb. 16, 2012.
PCT International Search Report and Written Opinion for PCT/US2010/054089 dated Feb. 16, 2012.
PCT International Search Report and Written Opinion for PCT/US2010/054085 dated Feb. 23, 2012.
PCT International Search Report and Written Opinion for PCT/IB2008/050102 dated Jun. 9, 2008.
PCT International Search Report and Written Opinion for PCT/US2010/054079 dated Feb. 23, 2012.
PCT International Search Report and Written Opinion for PCT/US2011/033429 dated Jun. 1, 2011.
PCT International Search Report and Written Opinion for PCT/US2011/057104 dated Feb. 21, 2012.
R.E. Lobnig et al, "Development of a new experimentatl method to determine critical pigment-volume-concentrations using impedance spectroscopy", Progress in Organic Coatings 55 (2006) 363-374.
J. Jachowicz et al., "The effect of the amphipiotic nature of human hair keratin on the adsorption of high charge density cationic polyelectrolytes", Colloid and Polymer Science 263: 847-858 (1985).
S.H.M. Gibson et al., "Determination of the critical pigment volume contrations of pigmented film coating formulations using gloss measurement", International Journal of Pharmaceutics 45, (1988) 245-248.
Masaki Okazaki et al., "Introduction of cationic groups onto carbon black surface and their dispersibility in water", J. Dispersion Science and Technology 21(5), 511-524 (2000).

* cited by examiner

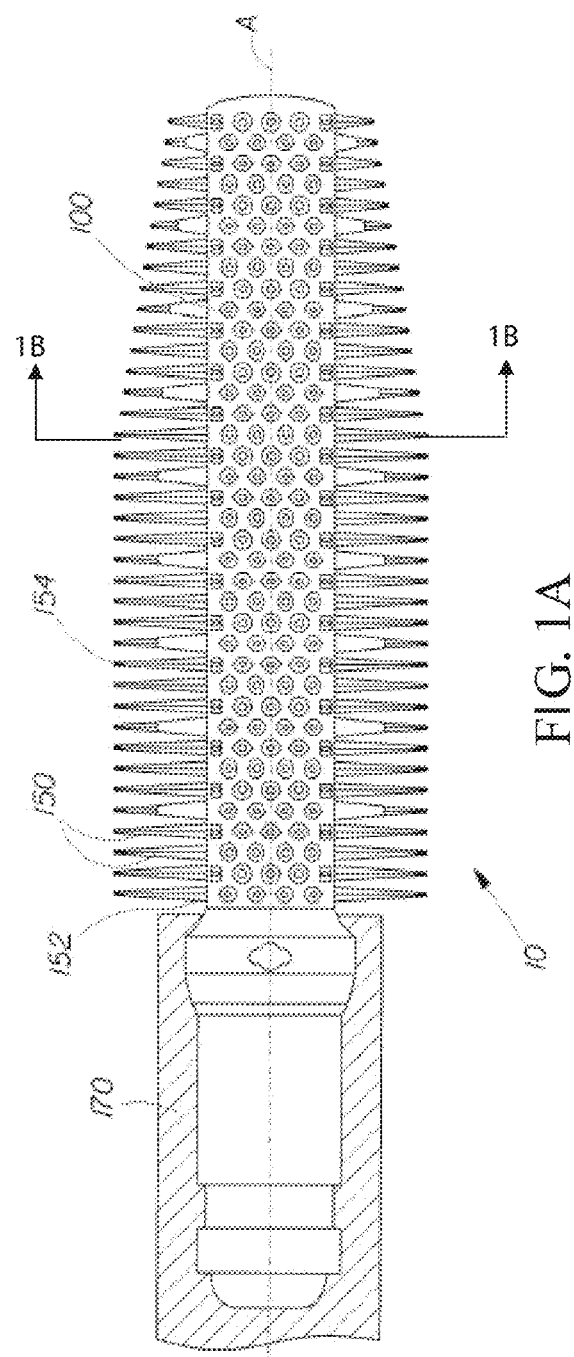

TWO-STEP MASCARA PRODUCT

CROSS REFERENCE TO RELATED APPLICATION

This application is a continuation-in-part of U.S. Ser. No. 13/274,852, filed on Oct. 17, 2011, which claims the benefit of U.S. Provisional Application No. 61/455,843, filed Oct. 27, 2010, and a continuation-in-part of U.S. Ser. No. 12/912,478, filed on Oct. 26, 2010, which claims the benefit of U.S. Provisional Application No. 61/255,457, filed Oct. 27, 2009, all of which are incorporated herein by reference in their entirety.

FIELD OF THE INVENTION

The present application is directed, generally, to a two-step, long-wear mascara product. Specifically, there is disclosed a first, long-wear mascara composition for use as a topcoat over a second, base coat mascara composition, which provides an improved aesthetic benefit to the eyelashes of a user when used in a two-step process.

BACKGROUND OF THE INVENTION

Mascaras are a major cosmetic product of significant importance to the cosmetic industry. They are used to enhance the beauty of a person's eyes by coating the eyelashes, and in some cases, the eyebrows, to primarily thicken, lengthen, color, curl, and define the individual lashes. There are a variety of mascara formulations including anhydrous formulations, water-in-oil emulsions, oil-in-water emulsions, and water-based mascaras, which may contain little or no oil phase. Oil-in-water emulsion mascara formulations typically contain emulsified waxes and polymers, with pigments dispersed into the water phase. The water may provide suitable application properties, while the waxes and polymers help provide transfer resistance to mascara film formed on the lash. Anhydrous and water-in-oil mascaras are sometimes referred to as waterproof mascaras, as they have superior transfer resistance, especially to water. Their high content of hydrophobic materials creates a film which contains very little materials that allow water to break up the film and make it wear away. In the case of the water-in-oil mascaras, the internal droplets of water can deliver water-soluble/dispersible materials that would otherwise not be able to be incorporated into an oily phase. The water-based mascaras are typically gelled water with a polymer to create deposition and hold of the lashes.

Consumers typically expect particular properties from their mascara products such as adhesion to the lashes, lengthening/curling of the lashes, lack of smudging or flaking, thick lashes, and good separation of clumps of lashes. Particularly, the desire is for long, luscious, full, soft, and separated lashes. Mascaras generally distribute a smooth and relatively thin (coating thickness) film over the eyelashes producing a satisfactory array of reasonably separated lashes that are darker and thicker than bare lashes, making the eyes more noticeably beautiful. While mascara may provide a variety of cosmetic benefits, at least some consumers find gloss, color and volume to be particularly important. In order to provide suitable gloss and color, the mascara should form a smooth, continuous film on the eyelash. A film that has a rough or discontinuous surface tends to scatter or fragment the light that reflects off of the eyelash, resulting in an undesirable dull or matte look. Typically, thinner films will usually form a smoother, more continuous surface than thicker films. This is due, at least in part, to the lack of large particles, which are commonly used to thicken a mascara composition.

In contrast, mascaras that form thick films on the eyelashes are typically perceived by consumers to increase the volume of the eyelashes (i.e., "volumizing" mascaras). That is, the user perceives an increase in the thickness of the eyelash along its length (although not necessarily uniformly). However, the presence of the large particles used to thicken these films (i.e., increase the viscosity) may form discontinuities in the surface of the film (e.g., cracks, hills, valleys and the like) that reduce the perceived gloss and color of the mascara. In addition, thicker mascaras are lead to increased clumping, which is the opposition of lash separation. Clumping occurs when adjacent eyelashes stick together and form clumps. Clumping is undesirable because it may give an observer the impression that the user has fewer lashes.

Over the course of a day, conventional mascaras typically wear off relatively quickly, especially when subjected to physical abrasion. Thus, reapplication throughout the day may be necessary. However, there may not be a convenient time or place for the user to reapply the mascara. As a result, these users may sacrifice the look they desire because they simply do not have the time or the desire or continually reapply mascara. In addition, even though conventional mascara typically wears off over the course of a day, a small amount may remain at the end of the day when the user goes to sleep. If this small amount of mascara remaining on the eyelashes at night is not removed, it may be undesirably transferred onto a sleeping surface (e.g., pillows, sheets, covers, bed clothes).

"Long Wear" mascaras are known, and may overcome some of the issues related to maintaining a "newly applied mascara" look throughout the day without the drawbacks of reapplication. But "long" is a relative term, and while existing long wear mascaras are intended to reduce or eliminate reapplication throughout the day, they are generally not suitable for multi-day wear. In some instances, the conventional long-wear mascara may not even provide a suitable look for 24 hours. Another problem sometimes associated with at least some conventional long-wear mascaras is the lack of volume they impart to the eyelashes.

Mascara compositions are generally applied to a keratinous surface using an applicator, sometimes referred to as a mascara brush or comb. When using a brush, the mascara is typically removed from a reservoir by placing the brush in the mascara reservoir and removing it. Excess mascara is removed from the brush with a wiper that contacts the distal ends of the bristles of the mascara brush as the brush is removed from the reservoir. The mascara that remains on the brush tends to be disposed around the core of the brush or flow toward the core. When the brush is contacted with the eyelashes of a user, the bristles separate the eyelashes such that the separated eyelashes can come into contact the core of the brush to receive the mascara disposed thereon.

There are generally two types of mascara brushes: molded plastic brushes and twisted-wire brushes. Plastic molded brushes are commonly formed from a thermoplastic material in an injection mold or similar process. Molded brushes typically have bristles arranged uniformly in rows with relatively wide spaces between the bristles. Mascaras having a relatively higher viscosity, such as some conventional volumizing mascaras, work well with a molded plastic brush for high levels of look control because the larger spaces between the bristles of the molded plastic brush are suitable for receiving the thicker composition (i.e., the composition flows more easily between the bristles). In contrast to a molded plastic brush, the bristles of a twisted-wire brush are generally spaced more closely together, and generally do not form well defined rows. This reduced space between bristles results in more resistance to flow for a higher viscosity mascara composition. Twisted-wire brushes are typically formed by placing a plurality of bristles between two parallel metal wires and then twisting the wires together in a helical or helix-like (e.g., coiled or spiral) configuration to trap and hold the bristles between the wires. It is not uncommon for the bristles of a twisted-wire brush to appear to be randomly distributed on the core.

Accordingly, it would be desirable to provide a mascara product that lasts more than 24 hours and achieves the desired look of current mascaras and the consumer desired feel.

BRIEF DESCRIPTION OF THE DRAWINGS

FIG. 1A is a plan view of a molded plastic brush.

SUMMARY OF THE INVENTION

Figure 1B:
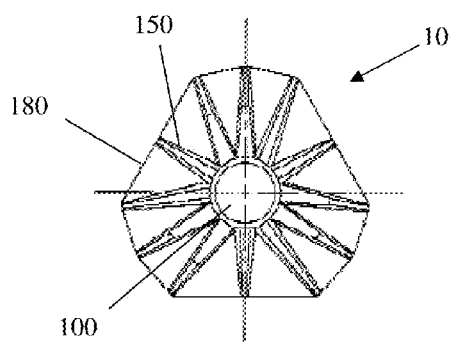
FIGS. 1B and 1C are alternative cross-section views of the applicator of FIG. 1A.

In order to provide a solution to the aforementioned problems, disclosed herein is a two-step mascara product comprising a first mascara composition and a second mascara composition. The first mascara composition includes a film-forming polymer dispersed in a first carrier, and the first mascara composition has a first viscosity. The second mascara composition includes from 10-80% by weight of a volatile second carrier and from 15-35% by weight of a film-former selected from the group consisting of tall oil glycerides, pentaerythrityl rosinate, glyceryl rosinate, hydrogenated versions of these and mixtures thereof. The second mascara composition has a second viscosity. The two-step mascara product also comprises a package for storing and dispensing each of the first and second mascara compositions. The package comprises a first container configured to store and dispense the first mascara composition and a second container configured to store and dispense the second composition.

DETAILED DESCRIPTION OF THE INVENTION

All percentages are by weight of the entire composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

Definitions

"Equivalent diameter" means the diameter of a circular particle or the diameter of the circle in which the cross-section of a non-circular particle is inscribed.

"Joined" means configurations whereby an element is directly secured to another element by affixing the element directly to the other element, and configurations whereby an element is indirectly secured to another element by affixing the element to intermediate member(s) that in turn are affixed to the other element.

"Keratinous tissue," means keratin-containing tissue layers disposed as the outermost protective covering of mammals which includes, but is not limited to, skin, hair, and nails.

"Large molded plastic brush" means a molded plastic mascara brush having a core diameter of greater than 3.0 mm (e.g., greater than 3.5 mm, 4.0 mm, or even 5 mm). In contrast, a small molded plastic brush means a molded plastic brush having a core diameter of less than 3.0 mm (e.g., less than 2.5 mm or even less than 2.0 mm).

"Large twisted wire brush" means a twisted wire brush having a maximum diameter of greater than 9 mm. In contrast, "small twisted wire brush" means a twisted wire brush having a maximum diameter of less than 9 mm.

"Mascara" and "mascara composition" mean a liquid cosmetic composition that is applied to eyelashes to provide an aesthetic benefit or change in appearance such as, for example, the appearance of a color change, a volume change, and/or a length change. Mascara may also be applied to eyelids, and/or eyebrows. The present mascara compositions are formulated for topical application to mammalian keratinous tissue for use in cosmetic products. The methods of using mascara compositions are also included within the meaning of mascara composition.

"Twisted-wire brush" means a brush for applying mascara to the eyelashes of a person characterized by a plurality of bristles securely held between at least two wire-shaped elements coiled around one another in a helical, helix-like, or braided configuration.

Two-Step Mascara Product

Disclosed herein is a two-step mascara product that includes a first mascara composition, that is intended to be used a base coat and a second mascara composition that is intended to be used as a topcoat. A more detailed description of the base coat and top coat is provided below. During use, a user applies the base coat to the eyelashes in a manner commonly used to apply mascara and subsequently applies the topcoat in the same or a different manner. Surprisingly, it has been found that a particular combination of mascara formulas and applicators when used in succession results in an unexpected improvement in the cosmetic benefit provided by the mascara. In particular, the use of the present two-step mascara products provides a more intense (i.e., darker and more lustrous) and consumer preferred look than either of the individual mascara compositions when used alone. Additionally, when used in combination, the base coat and top coat of the present mascara product provide improved and long-lasting volume, separation, gloss and color relative to conventional mascaras.

In some instances, depending on the base coat and top coat formulations, the top coat may be applied to the eyelashes immediately after applying the base coat. On the hand, it may be desirable to wait for short period of time to let the base coat dry before applying the top coat (e.g., at least 10 seconds, 30 seconds, 1 minute, 2 minutes or more).

The base coat and top coat of the present mascara product may be provided to a consumer in the same or separate packages. For example, the base coat and topcoat may be stored in separate reservoirs disposed at opposing ends of a dual-ended package. The base coat herein provides a suitable amount of volume and separation benefit to the eyelashes, while the topcoat provides a smooth, continuous film and a long-wear benefit. However, it is to be appreciated that the base coat and/or top coat are not necessarily limited to these benefits, but may each provide one or more additional cosmetic benefits commonly associated with the use of mascara.

Base Coat

The base coat herein is a mascara composition formulated such that, when combined with a suitable applicator such as one of the applicator brushes disclosed herein, it will deposit a thick coating of mascara onto keratinous fibers (e.g., eyelashes) thereby increasing the volume and/or length of the keratinous fibers. In order to provide a thick coating of mascara, which is important for providing the desired increase in volume, the base coat may include large primary particles, which have an equivalent diameter of more than 5 microns. In some instances, particles may be considered primary particles even if they initially have an equivalent diameter of less than 5 microns, but increase in size (e.g., swell) after application to keratinous fiber to an equivalent diameter of 5 microns or greater. Suitable primary particles sizes herein include between 5-100 microns (e.g., 10-75 microns or 15-50 microns). It is believed, without being limited by theory, that primary particles with an equivalent diameter of at least 5 microns enable a mascara film of from 5 to 100 microns thick to be deposited onto the eyelashes, which may provide a user with a perception of more noticeable lashes.

The primary particles of the composition may be solid, hollow, or porous; hydrophilic or hydrophobic; and have a shape that is, for example, spherical, oval, ovoid, platelet, star, rod, cubic or irregular. "Irregularly shaped" means any shape that is not spherical, oval, ovoid, star, rod or cubic. In some instances, the primary particles may be composed primarily of a hydrophobic material that will add bulkiness to the mascara coating and hold the curl of the lashes in place. Nonlimiting examples of primary particles suitable for use herein are disclosed in U.S. Pat. No. 7,632,489 to Wyatt, et al.

The primary particles may include a wax or combination of waxes in an amount of up to 40% by weight. Waxes are lipophilic fatty substances that are solid at room temperature (25° C.) and have an anisotropic crystal organization, but undergo a reversible solid-to-liquid change of state at a temperature of about 30° C. or more, up to about 150° C. In conventional mascaras, wax particles are typically emulsified or dispersed into the carrier vehicle, such that their "particulate" nature readily breaks down when the mascara is applied. Thus, the wax is no longer in the form of aggregated wax particles but as much smaller platelet-shaped sheets of wax that interlock together to form a relatively smooth film on the lash. In the present mascara composition, however, large wax particles (e.g., from 5-2000 microns in equivalent diameter) may be added to base coat mascara composition to provide suitable thickening characteristics. The melting point of the large wax particle must be sufficiently high and the particle must be introduced into the mascara formulation at a sufficiently low temperature that it does not soften due to the process temperature or interactions with other materials in the formulation. The wax particle should retain at least some to most of its size and shape by visual observation during addition into the composition and during application to keratinous fiber such that it maintains its bulkiness even after being applied to the keratinous fiber. Waxes suitable for use herein may have a melting point of greater than 40° C., 50° C., or even 55° C.

Nonlimiting examples of suitable waxes include animal waxes, vegetable waxes, mineral waxes, synthetic waxes and mixtures thereof. In particular, exemplary waxes include beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); C24-45 alkyl methicones (silicone waxes); waxes obtained by catalytic hydrogenation of oils chosen from animal, plant, and synthetic origins comprising at least one fatty chain chosen from linear and branched C8-C32 fatty acids (e.g., hydrogenated jojoba oil, hydrogenated sunflower oil, hydrogenated castor oil, hydrogenated coconut oil, and hydrogenated lanolin oil); and mixtures thereof.

In some instances, the primary particles may include thermoplastic and/or thermoset polymeric particles that have, for example, a molecular weight of from about 2000 to about 25,000,000 and are capable of forming a suitable film. When a thermoplastic polymer particle such as polypropylene is used, it may be desirable to use polymers that have a glass transition temperature (Tg) of no less than about −150° C. (e.g., no less than about −130° C.) and no more than about 300° C., (e.g., no more than about 200° C.). It may be desirable to combine the polymer with a plasticizer to adjust the properties of the polymer. Plasticizers are materials applied to a polymer to soften or improve its flexibility. In the case of a mascara composition, a plasticizer may help the polymer particle to partially deform when applied to lashes, creating a smoother, more flexible mascara film. Suitable polymeric particles will retain much of their shape and bulkiness once they are applied to a keratinous fiber.

The base coat composition herein may also include secondary particles to provide benefits such as preservation, opacity, coating smoothness, color, transfer resistance, rheological modification, and/or lash separation. For example, the composition may include pigment particles such as iron oxides to impart color to the mascara film. In some instances, the secondary particles may include latex particles to impart transfer resistance to the mascara. Different sizes and/or shapes of secondary particles may be selected to provide a smoother film surface. For example, platelet-shaped (e.g., 25 micron equivalent diameter) and spherical (e.g., 20 micron equivalent diameter) secondary particles may be combined to create a smoother mascara film. In some instances, smaller secondary particles (i.e., secondary particles that have an equivalent diameter that is less than the equivalent diameter of the primary particles) may be used to fill in void space between the primary particles. For example, 5 micron secondary particles may be used to fill in void space between 40 micron primary particles to provide a smoother mascara film. In this example, the primary particles may have a shape that is the same as or different from the secondary particles (e.g., one or both types of particles may be spherical).

In some instances, the secondary particles may be fibers which enable the improvement of volume and/or lengthening of lashes by the mascara. The term "fiber," as used herein, means an object of length L and diameter D such that L is greater than D, wherein D is the diameter of the circle in which the cross section of the fiber is inscribed. For example, the ratio L/D (or shape factor) may be from at least about 3.5:1 or from about 5:1 but no more than about 500:1 or no more than about 150:1. The fibers that may be used in the composition may be chosen from mineral and organic fibers of synthetic or natural origin. The fibers may be short or long, individual or organized, such as being braided, and hollow or solid. They may have any shape, such as a circular or polygonal (square, hexagonal, or octagonal) cross section, depending on the intended specific application. For example, their ends may be blunt and/or polished to prevent injury. The fibers may have a length of at least 1 micron (e.g., at least 50 microns or 90 microns) but no more than 5 mm (e.g., no more than 1 mm or no more than 100 microns). The weight or yarn count of the fibers may be given in units of denier, and represents the weight in grams per 9 km of yarn. Suitable fibers may have a yarn count of from 0.15 to 30 denier or from 0.18 to 18 denier. The fibers may be treated or untreated at the surface and coated or uncoated. If coated fibers are used, non-limiting mention may be made of polyamide fibers coated with copper sulphide, which may provide an antistatic effect (for example R-STAT from Rhodia), or another polymer which may enable a particular organization of the fibers (specific surface treatment), or surface treatment, such as color/hologram effects (Lurex fiber from Sildorex, for example).

In some instances, the fibers may be "rigid" fibers that do not undergo a substantial change in shape when placed in a dispersing medium. The rigid fibers may be straight and linear. Exemplary rigid fibers include those formed from synthetic polymers such as polyesters, polyurethanes, acrylic polymers, polyolefins, polyamides, such as non-aromatic polyamides, and aromatic polyimideamides. For example, the rigid fibers may be chosen from aromatic polyimideamide fibers. Further for example, polyimideamide yarns or fibers that may be used for the compositions of the invention are described, for example, in the document from R. Pigeon and P. Allard, Chimie Macromo-culaire Applique, 40141 (1974), pages 139-158 (No. 600), or in U.S. Pat. No. 3,802,841, or in documents FR-A-2 079 785, EP-A1-0 360 728 and EP-A-0 549 494.

The primary and, optionally, secondary particles in the base coat help provide a desirable volume and/or length increasing benefit when applied to the eyelashes of user, but the addition of these particles may result in a thicker mascara composition. The base coat may have a viscosity in the range of 350,000-1,000,000 centipoise ("cps"), 400,000-800,000 cps, or 425,000-575,000 cps as measured by Brookfield brand RTV viscometer using a type TE spindle at 10 rpm and 25° C. Because of the relatively high viscosity of the base coat, it is important that an applicator be selected that provides sufficient core surface area and bristle distribution to enable a thicker mascara composition, which may not be particularly flowable, to be applied as desired. Suitable examples of base coat formulations and applicators for use with the present base coat are described in U.S. Pat. No. 7,632,489 to Wyatt, et al. and U.S. Publication No. 2008/0115798 filed by Rainey, et al.

Carrier

The base coat may include a dermatologically acceptable carrier. The carrier can be volatile or nonvolatile and includes compositions that dissolve or uniformly disperse the primary and, optionally, secondary particles. Suitable carriers include, but are not limited to, water, lower alcohols (such as ethanol, isopropanol), dihydric alcohols such as propylene and butylene glycol, polyols such as glycerin, hydroalcoholic mixtures, hydrocarbons (such as isobutane, hexane, decene, acetone, isododecane, and straight or branch chained hydrocarbons having about 8 to about 20 carbon atoms), halogenated hydrocarbons (like Freon), linalool, hydrocarbon esters (such as ethyl acetate, dibutyl phthalate), volatile fluids, phenethyl pentamethyl disiloxane, methoxypropyl heptam-ethyl cyclotetrasiloxane, chloropropyl pentamethyl disiloxane, hydroxypropyl pentamethyl disiloxane, octamethyl cyclotetrasiloxane, decamethyl cyclopentasiloxane), volatile dimethicone, and mixtures thereof.

Film-Former

The base coat may include a film-former such as a film-forming polymer. "Film-forming" means the ability to form a film when the composition is spread on glass. Film-forming polymers suitable for use herein may be water-soluble or water-dispersible polymers. Examples of water-soluble polymers include, but are not limited to, polyvinylpyrilidone and polyvinyl alcohol. Examples of water-dispersible polymers are ammonium acrylates copolymer and polyurethane. The film-forming polymers may also be oil soluble. Examples of oil soluble film-forming polymers include, but are not limited to, organosiloxane resins having a number molecular weight average range of from about 1,000 g/mole to about 10,000 g/mole (e.g., trimethylsiloxysilicate, dimethicone, and hydrogenated polycyclopentadiene).

Top Coat

The top coat herein is a mascara composition formulated such that, when combined with a suitable applicator brush such as one of the applicator brushes disclosed herein, it will deposit a coating of mascara onto the eyelashes and base coat, thereby providing a smooth, glossy film of mascara. In particular, it is believed, without being limited by theory, that formulating the top coat composition to have a viscosity that is less than the viscosity of the base coat, and which can be suitably applied with a twisted brush, is important for providing a smooth, continuous mascara film that exhibits a synergistic color and/or volume benefit. In addition, the top coat enables the two-step mascara product to remains intact on the eyelashes and/or eyelids of the wearer for greater than 24 hours (e.g., 36 hours, 48 hours or more), but typically less than five days.

Some mascara formulations such as the base coat above may include a large amount of wax(es) (5-15%) and iron oxides (6-12%) while using relatively small amounts of film formers (4-8%). The films formed by such mascara compositions are generally defined by the waxes present in the composition, which can have crystal sizes in excess of 20 microns and appear jagged and rough when viewed under magnification. Further, some conventional pigments used in mascara formulations may also have a relatively large particle size, for example, widely distributed in the 2-5 micron range. It is known that the properties of a film are directly related to the volume concentration of solids it contains, which may be characterized by the concept of critical pigment volume concentration ("CPVC"). The CPVC is the point at which there is just enough film-former matrix to wet and fill the voids between individual particles. At solids volume concentrations above the CPVC, the film-former matrix is no longer a continuous phase. Studies have shown that the pigment volume concentration impacts many film properties, including gloss, film flexibility, and abrasion resistance. As the pigment volume concentration increases, film flexibility decreases and abrasion resistance remains the same or improves. When the CPVC is exceeded, the film will become brittle and abrasion resistance will decrease rapidly. Gloss also decreases as the pigment volume concentration increases and remains low when the CPVC is exceeded. Because some mascaras use pigments with relatively large particle sizes and a relatively low amount of film former, they tend to have a solids volume concentration in excess of the CPVC. As a result, conventional mascara films exhibit poor abrasion resistance and often are brittle films that flake easily.

The semi-permanent top coat herein has a volume concentration of solids that is below the CPVC. This may be achieved in two ways. First, only small particle size solids should be used for the pigments and thickeners. For example, using a thickener of only disteardimonium hectorite clay particles (D90<10 microns) at from 10% to 15% by weight of the semi-permanent mascara composition and a pigment formed from jet milled iron oxide particles (D90<1 micron) present at from 7% to 10% by weight of the composition may provide a formulation with a solids concentration level that is below the CPVC. Second, a greater level of film formers may be used (e.g., from 17 to 30%). Because the solids volume concentration of the film is below the CPVC, it generally exhibits greater resistance to flaking and transfer caused by stretching and abrading than conventional mascara compositions. Surprisingly, the present semi-permanent mascara composition forms a continuous film that provides a relatively smooth film surface with a glossy, dark appearance. Suitable ratios of film former to particles in the present top coat include from 2:3 to 100:1 (e.g., 1:1-50:1, 1:2-30:1, or 1:3-20:1).

In addition to a suitable CPVC, it is important for the top coat to have a suitable viscosity so that the proper applicator (i.e., brush), which is discussed in more detail hereinbelow, can be provided in a commercial product. Suitable viscosities for the present top coat are in the range of 50,000-350,000 cps, 150,000-300,000 cps, or 225,000-275,000 cps as measured by Brookfield brand RTV viscometer using a type TE spindle at 10 rpm and 25° C.

FIG. 1 illustrates an exemplary film 100 formed by the present top coat. The film 100 includes suitably spaced pigment particles 110 and thickener particles 120 dispersed in a matrix of film former(s) 130. The pigment particles may all be the same type and/or color of pigment or two or more different pigment types (e.g., organic and inorganic) and/or colors. Additionally or alternatively, the film 100 may include other types of colorants such as, for example, lakes and dyes. In some instances, the top coat may not include any colorants. The film 100 may include a thickener (e.g., colloidal particles or wax). The film 100 may be formed from an anhydrous dispersion of pigment 110 and thickener 120 in a film-former matrix 130, along with one or more volatile carriers. One particularly suitable example of a top coat composition is an anhydrous dispersion of rosin esters as film-formers, iron oxides as colorants, and isododecane as a volatile carrier. In this example, it may be desirable to also include a clay network (e.g., bentone clay) to stabilize the matrix.

Figure 1C:
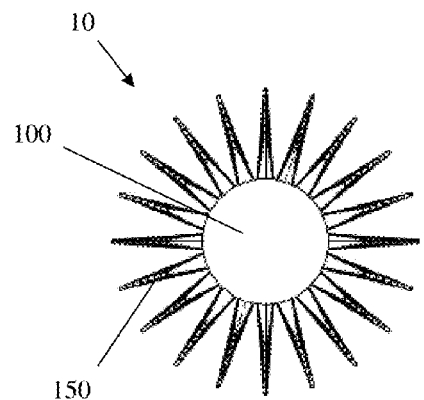
Figure 2:
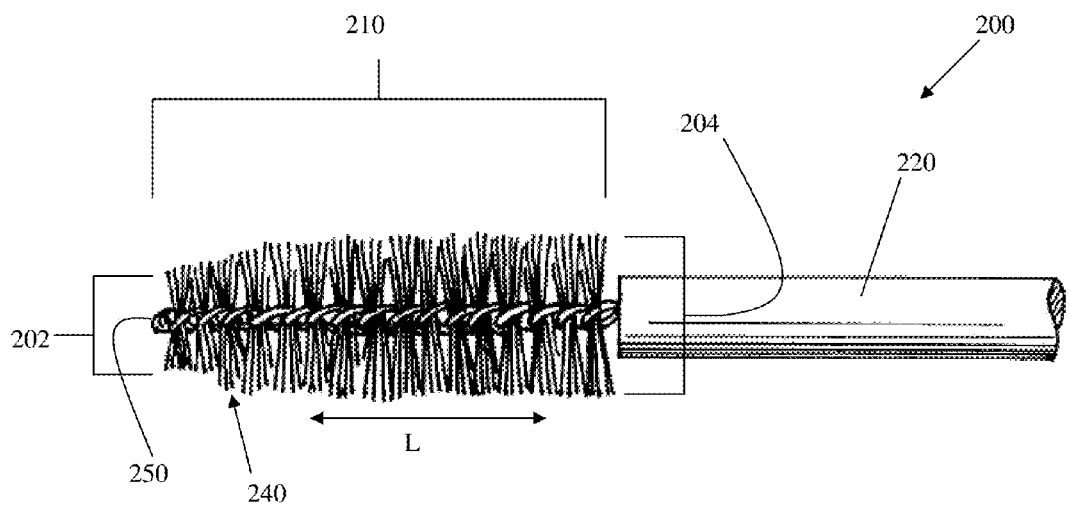
FIG. 2 is a plan view of a twisted wire brush.

FIG. 2 illustrates a film 200 formed from a mascara composition that includes large particles and/or has a solids concentration that is greater than the CPVC. The film 200 includes spaced pigment particles 210 and thickener particles 220 dispersed in a matrix of film formers 230. But unlike the film 100 illustrated in FIG. 1, the film 200 in FIG. 2 also includes relatively large wax particles 240 disposed in the matrix, which impart undesirable characteristics to the film 200.

Film-Former

The present top coat includes a film-former. The film-former is selected to provide a smooth continuous film on the target surface (e.g., eyelashes and/or base coat) and a matrix in which the particulate components of the mascara may be suspended. Particularly suitable film formers include rosin esters, which are derived from rosin and are commonly used as tackifiers in commercial adhesives (e.g., hot melt adhesives and pressure sensitive adhesives). Rosin is a sustainable, solid form of resin obtained from conifers (e.g., pine tree sap). Rosin is known to include a mixture of closely related rosin acids, especially abietic acid, characterized by three fused six-carbon rings, C=C double bonds that vary in number and location, and a single carboxylic acid group. Commercial methods for obtaining rosin are also known and include, e.g., distilling the volatile turpentine from oleoresin exuded from the wound of living pine trees to obtain gum rosin, or the chemical separation of tall oil, which is a byproduct of the wood pulp industry, to obtain tall oil rosin. The carboxylic acid group of a rosin acid can be converted to an ester by reacting the acid with an alcohol. Esterification of rosin modifies the softening point, adhesiveness, cohesiveness, and melted viscosity of the material. The alcohols typically used to make rosin esters are methanol, tri-ethylene-glycol, glycerol, and pentaerythritol. Tall oil rosin is esterified with glycerol to form tall oil glycerides, a mixture of rosin acids, and esters of glycerol. Tall oil glycerides are available from, for example, Arizona Chemical Co. Glyceryl rosinate, is the ester of a rosin acid reacted with glycerol. Pentaerythrityl rosinate, sometimes referred to as pentaerythritol rosinate, is the ester of a rosin acid reacted with pentaerythritol. Pentaerythritol rosinate is commonly used as a skin conditioning agent-emollient and viscosity increasing agent, and is nonaqueous in cosmetic formulations.

Rosin includes a conjugated system of C=C double bonds, which makes it susceptible to oxidation, isomerization and other chemical reactions. A common method to improve stability is to hydrogenate the rosin, for example, by the addition of hydrogen to the conjugated C=C double bonds in the presence of a catalyst to form saturated ring structures. Hydrogenated rosin esters have specific advantages over non-hydrogenated (e.g., lighter color, improved stability, and reduced skin sensitization). The hydrogenated versions of pentaerythrityl rosinate and glyceryl rosinate (i.e., pentaerythrityl hydrogenated rosinate ("PHR") and glyceryl hydrogenated rosinate ("GHR")) are suitable for use herein.

Film-formers such as tall oil glycerides, pentaerythrityl rosinate, PHR, glyceryl rosinate, and GHR are present in the top coat in significantly higher concentration than previously used in conventional mascara. When used in conjunction with conventional mascaras, rosin esters are typically present in amounts of less than 5%. This is because the rosin in conventional mascaras is used as a tackifier to provide improved adhesion to the eyelash and water-resistance and not as a film-former. Before now, it was thought that rosin esters were unsuitable for use as a film-former in a mascara product because of their tackiness and poor spreadability. Surprisingly, the top coat herein may include 15% or more of a rosin ester (e.g., 17% or even 20% or more, but typically less than 35%), by weight of the film-former and still provide suitable spreadability. Suitable rosin esters for use in the top coat include tall oil glycerides, pentaerythrityl rosinates, glyceryl rosinates, and the hydrogenated versions and mixtures thereof.

Carrier

The top coat may include a carrier to help deliver the desired mascara components (e.g., pigments and film-formers) to the eyelash or eyelid. In certain embodiments, the semi-permanent mascara composition may include a volatile carrier that quickly volatilizes from the surface of the eyelashes or eyelid, leaving the desired components behind. The volatile carrier may be present at 10% to 85%, 15% to 80%, or even 20% to 70% by weight based on the weight of the composition. Nonlimiting examples of suitable volatile carriers include volatile hydrocarbons, volatile silicones, and mixtures thereof. The ratio of film-former to volatile carrier may be controlled such that the dried film consists of from 30% to 70%, 40% to 60%, or even 50% film former by weight.

Hydrocarbon oils suitable for use as a carrier in the present mascara compositions include those having boiling points in the range of 60-260° C., such as hydrocarbon oils having a carbon chain length of from C8 to C20 (e.g., C8 to C20 isoparaffins). Particularly suitable examples of isoparaffins include those selected from the group consisting of isododecane, isohexadecane, isoeicosane, 2,2,4-trimethylpentane, 2,3-dimethylhexane and mixtures thereof. Isodecane is available from Presperse under the brand name Permethyl 99A and has the formula: $CH_3(CH_2)10CH$.

A volatile silicone fluid may also be used as a carrier herein. Suitable volatile silicone fluids include cyclomethicones having 3-, 4- and 5-member ring structures corresponding to the formula:

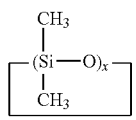

where X is from about 3 to about 6. Nonlimiting examples of commercially available volatile silicones include 244 Fluid, 344 Fluid and 245 Fluid, and/or 345 Fluid from Dow Corning Corporation.

Colorants

The base coat and/or top coat may include colorants such as dyes, pigments, lakes, and mixture thereof. In some instances, the top coat and/or base coat may include from 0.1-70% (e.g., 0.5-50% or 0.5-35%) by weight of a colorant. Colorants in the form of particles having average diameters of 0.1 to 10 microns may be acceptable for use in the present compositions (e.g., 0.1 to 5 microns or even 0.1 to 1 microns). It may be desirable to select colorant particles with a diameter that is less than the thickness of the mascara composition drieddown film, especially for the top coat. The small size of the colorant particles may allow them to be fully encased in the dried film, which may result in a smoother film.

Suitable colorants include organic or inorganic pigments approved for use in eye-area cosmetics by CTFA and/or the FDA. Exemplary inorganic pigments include particles of iron oxides (e.g., yellow, brown, red, black), titanium dioxides, iron sulfides, ultramarines, chromium oxides (e.g., green) or other conventional pigments used in cosmetic formulations. Examples of organic pigments include D&C Black No. 2, D&C Black No. 3, FD&C Red No. 40, D&C Green No. 5, FD&C Blue No. 1, and FD&C Yellow No. 5. Examples of lake dyes include various acid dyes which are laked with aluminum, calcium or barium. Additional colorants for use herein include annatto, caramel, carmine, β-carotene, bismuth oxychloride, ferric ammonium ferrocyanide, ferric ferrocyanide, chromium hydroxides (e.g., green), guanine, mica, aluminum powder, bronze powder, copper powder, manganese violet, zinc oxide. Suitable colorants along with their chemical structure are described in, e.g., 21 C.F.R. Part 74 and in the CTFA Cosmetic Ingredient Handbook, (1988), published by the Cosmetics, Toiletry and Fragrances Association, Inc. Other colorants may also be used as they are developed and determined safe.

Encapsulated colorant microparticles having average diameters of 0.1 to 10 microns may be acceptable for use in the present semi-permanent mascara compositions. Suitable examples of encapsulated colorant microparticles are disclosed in copending U.S. Publication Nos. 20090263658 and 20090271932A1. The encapsulated colorant microparticles may comprise from 1 to 60% by weight of at least one colorant, for example 5% to 40% or even 7% to 25% by weight. Microencapsulated colorants may provide a more vibrant color to products used around the eye area, including eyelashes. The primary colors are understood to mean red, yellow and blue. An additional feature of microparticles is the elimination of milling or grinding often encountered with non-encapsulated colorants.

Colorants that are surface modified with a hydrophobic coating (e.g., triethoxycaprylsilane) may be acceptable for use herein. Hydrophobically coating colorants such as pigment particles may increase their dispensability in the nonpolar solvent and increase their resistance to being washed off during exposure to showering and facial cleansing.

Thickeners

The top coat and/or basecoat may be thickened or structured with colloidal particles and/or waxes. Suitable thickeners include waxes such as carnauba wax, candellila wax, beeswax, and polyethylene wax; particles such as disteardimonium hectorite, kaolin, silica, and magnesium carbonate; polymers; viscous hydrocarbons; and combinations thereof. When present in the top coat, the waxes may be selected to maintain the film durability of the mascara composition. In some instances, the wax may be present at from 3-15% (e.g., from 4-10% or from 5-8%) by weight. In some instances, it may be desirable to include wax at an amount of less than 3.0%, for example, less than about 1.0% or eve less than 0.1%, by weight, of wax and wax like components. In some instances, the top coat and/or base coat may be free of wax.

Disteardimonium hectorite is a particularly suitable thickener to build structure/viscosity in a mascara composition. When present in the top coat, disteardimonium hectorite may help provide suitable spreading/deposition across lashes and ensure adequate stability/suspension of colorant particles in the dispersion over time. The diameter of the disteardimonium hectorite particles should be smaller than the thickness of the mascara composition dried-down film (e.g., less than 10 microns). The present mascara compositions may from about 1% to about 25% of suitable thickener such as disteardimonium hectorite, from about 2% to about 20%, or even from about 3% to about 15%.

Actives

The top coat and/or base coat may include a safe and effective amount of a biological, chemical, nutraceutical, or pharmaceutical active, or a combination thereof. Biological actives may include prostaglandins, antimicrobials, antibacterials, biocides, preservatives, proteins, amino acids, peptides, hormones, growth factors, enzymes (e.g., glutathione sulphydryl oxidase, transglutaminase), therapeutics, oligonucleotides, genetic materials (e.g., DNA, RNA), and combinations thereof. Chemical actives may include dyes, surfactants, sensates, hair conditioners, hair dyes, hair growth agents, hair removers, hair growth inhibitors, hair styling gels, and combinations thereof. Nutraceutical actives may include proteins, preservatives, vitamins, food-additive materials, and combinations thereof. Pharmaceutical actives may include antibiotics, drugs, hair growth agents, hair removers, hair growth inhibitors, and combinations thereof.

Mascara Remover

High concentrations of PHR and tall oils may substantially reduce the solubility of a mascara composition in soap and water. Prior mascara formulations kept the concentration of these two components low to insure the mascara could be washed off in soap and water. Accordingly, it may be desirable to provide a solvent-based mascara-remover composition with the two-step mascara composition, for example, sold together as a kit or sold separately. The mascara remover may include at least 40%, 50%, and even at least 55% of a solvent selected from the group consisting of mineral oil, petroleum jelly, isododecane, silicones, other hydrocarbon solvents and mixtures thereof. In some instances, the mascara remover may include up to 100% of the solvent.

Applicator

A variety of conventional applicators are known in the art for use with mascara products (e.g., molded plastic applicators and twisted-wire brush applicators). Most mascara applicators take the form of a brush or comb that includes head disposed at one end of the applicator and a handle or similar graspable feature disposed at the opposing end. Typically a stem is used to join the handle to the head. The applicator head includes a core, which may be formed from twisted wire or molded plastic, both of which are described in more detail below. A plurality of bristles are disposed on the core and extend outwardly therefrom. The bristles may be formed from individual natural or synthetic fibers that are securely joined to the core in a random or semi-random configuration. Alternatively or additionally, the bristles may all be formed simultaneously from a plastic material, for example, in an injection molding process and securely joined to core in the same or a subsequent process to form an integral applicator head.

The primary method of depositing mascara onto the eyelashes of a user involves inserting the applicator into a supply of mascara, typically contained in a bottle or similar container, so that the mascara is deposited on the head (i.e., bristles and core) of the brush. Excess mascara is removed from the head of the brush, especially the outermost portions of the bristles spaced away from the core, via a wiper when the brush is withdrawn from the mascara container. Ideally, a suitable amount of mascara remains at least on the core of the brush for application to the eyelashes of a user. When the brush is used as intended, the lashes of a user are moved past the bristles of the brush via the spaces between the bristles such that the lashes come into contact with the mascara-containing core and, optionally, portions of the bristles (e.g., the inner portions). Thus, it is the characteristics of the mascara (e.g., coherent strength & rigidity) in combination with the applicator and wiper that provides the primary mechanism of product control and dosing.

In order to provide the desired volumizing and/or lengthening benefit to the eyelashes, it may be desirable to apply a relatively thick layer of the base coat composition to the eyelashes with a large molded plastic brush. A large molded plastic brush has a core with a relatively large surface area, which permits additional mascara to be held on the core. Moreover, the larger core of a molded plastic brush may facilitate a better and more even contact between the applicator and the lashes, which further promotes increased mascara transfer to the lashes. The molded plastic applicator may be configured with wide and uniform spacing between adjacent bristles in a row (i.e., along the length of the core). The bristles on a large molded plastic brush are spaced farther apart and more evenly spaced than a typical twisted wire brush, which tend to have bristles that are close to one another and randomly spaced apart. Thus, a thicker mascara composition such as the base coat herein may flow more easily between the bristles of a large molded plastic applicator to the core where the mascara can be contacted with the lashes and deposited thereon. In addition, the larger core permits the addition of a greater number of bristles, which aids in lash separation. A large molded plastic brush may have between 300 and 500 bristles arranged in longitudinal rows that are spaced uniformly around the core at, for example, 18 degree intervals. Of course, it is to be appreciated that the rows of bristles need not necessarily be spaced evenly around the core, but may be spaced as desired (e.g., at greater or less than 18 degrees). In contrast, a small molded plastic brush has a core with a smaller diameter than a large molded plastic brush and may have between 150 and 300 bristles arranged in rows spaced around the core. When used in conjunction with a relatively thick mascara product, a small molded plastic brush may not be able to provide the volume benefit and/or lash separation benefit that a large molded plastic brush can provide.

FIG. 1A illustrates a plastic molded applicator 10. The applicator 10 comprises a substantially longitudinal thick core 100 having a longitudinal axis A, and a plurality of bristles 150 extending from, or through, the surface of the core 100. Each bristle 150 has a base 152 associated with the core 100 and a free end or tip 154 opposite to the base 152. Each bristle 150 has external walls. The walls of the bristle 150, extending along either the bristle's entire length or any portion thereof can be straight (shown in FIG. 1), concave, round, planar, convex, or irregularly shaped. The bristles 150 may be solid, hollow or partially solid throughout their thickness and length. The bristles 150 can have a length equal to, or less than, an equivalent diameter of the core 100. The applicator 10 may have at least twelve rows of bristles 150 (e.g., 12-32, 14-28, 16-24, or even 18-22). The applicator 10 may have at least twelve bristles 150 per row (e.g., 14-24 or 18-22). The distance between two adjacent bristles 150 (i.e., clearance therebetween) can be at least 0.4 mm (e.g., 0.5-1.0) mm, as measured at the bases 152 of the bristles 150. The equivalent diameter of an individual bristle 150 at its base 152 can be from 0.4 mm to 0.6 mm. It should be noted that these equivalent bristle diameters may differ among the plurality of bristles 150, if so desired.

FIG. 1B shows a cross-section view of the molded plastic applicator 10 of FIG. 1A along line 1B-1B. As illustrated in FIG. 1B, bristles 150 of different lengths are arranged unevenly around the circumference of the core (i.e., the angle between adjacent bristles is not the same for all bristles). An imaginary line 180 drawn between the free ends 154 of adjacent bristles 150 may be straight, concave or convex. FIG. 1C shows an alternate cross-section view of the molded plastic applicator 10 of FIG. 1A along line 1B-1B. As illustrated in FIG. 1C, bristles 150 of the same length are disposed evenly around the circumference of the core 100.

In order to provide a smooth, continuous mascara film on the eyelashes, it may be desirable to apply the top coat with a small twisted wire brush. When applying a lower viscosity mascara such as the present top coat it is important that the spacing of the bristles provide suitable product retention on the applicator as well as the desired amount of lash separation/clustering. A lower viscosity mascara formula will typically exhibit increased flowabilty and lower cohesive structure/strength than a thicker mascara composition such as the present base coat. Thus, the applicator bristles and/or inter-bristle spaces must provide suitable adhesion and capillary action to retain the mascara on the applicator head prior to application (e.g., to prevent dripping, running, or pooling) and still provide the desired application experience (e.g., smooth, uniform application of mascara to the eyelashes).

FIG. 2 shows a twisted-wire brush applicator 200. The twisted-wire brush 200 includes a brush head 210 joined to a stem 220, which may in turn be joined to a handle graspable by a user. The head 210 includes a twisted-wire core 250 and a plurality of bristles 240 joined thereto and extending outwardly therefrom. In some instances, the brush head 210 may be tapered. For example, as illustrated in FIG. 2, the brush head 210 tapers from a maximum diameter 204 to a minimum diameter 202, which are defined by the lengths of the bristles when the brush head 210 is viewed in a cross-section. The twisted-wire brush 200 may be include a plurality of bristles 240 (e.g., from 400 to 800 or any suitable number in this range) placed between two parallel wires, which are in a side-by-side, co-planar arrangement. Individual bristles may be positioned in single-file between the wires, or groups of bristles may be arranged in discrete clusters spaced apart from one another. The number and/or spacing of the bristles is important to provide sufficient capillary pressure to receive and hold the mascara composition on the core of the brush, but still allow the eyelash of the user to pass between the bristles to contact the mascara disposed on the core. In addition, the bristle number and/or spacing may be selected to provide desirable eyelash separation during use. The bristles may be the same or different lengths and portions of the bristles may extend lengthwise equidistantly out of the top and bottom surfaces of the plane defined by the parallel wires, or in any suitable proportional combination desired (e.g., 60/40 top/bottom; 70/30; 80/20; 90/10; or even 0/100). The parallel wires may then be coiled around one another to form a twisted-wire core 250 in which the plurality of bristles 240 are securely held.

The twisted wire brush 200 may include a twisted wire core 250 and/or brush head 210 having a length of between 15 and 32 mm (e.g., between 24 and 26 mm). The twisted wire core 250 may have between 10 and 30 turns (e.g., 17 to 19) and/or between 0.6 and 1.0 turns/mm (e.g., 0.66 to 0.77). The brush head may have a uniform cross-section or a non-uniform cross section. The bristles may be solid, hollow, or a combination thereof. The bristles may have the same or different lengths, for example, between 2.5 and 9 mm.

The core and bristles may be formed from any suitable material known in the art. For example, the core may be formed from aluminum wires and the bristles may be formed from a natural or synthetic fibrous material such as plant fiber or polypropylene fibers. It is to be appreciated that while fibrous bristles may be formed from thermoplastic materials such as polypropylene, they do not include bristles that are formed in well-known injection molding processes (or other similar processes), wherein one or more molten thermoplastic materials are used to form the bristles and core of the brush as a unitary structure or to form the bristles as a sleeve that is placed over the core. Suitable examples of materials for making the twisted-wire core and the bristles are disclosed in U.S. Pat. No. 5,490,529 to Karl, filed Jan. 18, 1994.

In some instances, it may be desirable to use a small twisted wire brush to apply the top coat of the present two-step mascara product. A small twisted wire brush is characterized as having a brush head with a maximum diameter of less than 9 mm (e.g., less than 8 mm, 7 mm, 6 mm, 5 mm or even less than 4 mm). This can be accomplished by selecting bristles of the corresponding length or by selecting bristles of a different length and arranging them in an offset pattern. It is well known that the bristles of a twisted wire brush are not as uniformly arranged as, for example, a molded plastic brush, and thus they may not penetrate the lashes effectively. Since the mascara to be applied to the eyelashes is primarily on the core of the brush, longer bristles coupled with a lack of uniformity means that the ability to physically contact the eyelashes with the product at the core is more difficult than with the smaller twisted wire brush. Using a smaller twisted wire brush to apply the top coat of the present two-step product provides a smoother and more continuous film than if applied with a large twisted wire brush, which results in an improved color and volume benefit on the eyelashes.

An exemplary small twisted wire brush for use herein may have a tapered brush head with a maximum diameter of less than 9 mm (e.g., from 6-8 mm or 7-8 mm) and a minimum diameter of less than 5 mm (e.g., from 2-6 mm or from 3-5 mm).

Package

The two-step mascara product may include a container (e.g., bottle or the like) suitable for storing and dispensing a mascara composition such as the top coat and/or base coat herein. The package may also include an applicator for transferring the top coat and/or base coat from the container to the eyelashes of a user. The package may be configured as two discrete containers joined to one another or to a common structural feature to form a unitary package. For example, the package may include threads or other mechanical means for removably and reattachably joining the containers to a common structural feature such as a hollow ferrule. In this example, when a container is joined to the hollow central ferrule, it forms a liquid impermeable barrier to prevent mascara from leaking or spilling out of the container. In some instances, two discrete containers, one of which includes the base coat and the other the top coat, may be sold separately or together. In some instances, the base coat and top coat may be stored in a single container that includes two or more internal storage spaces configured to keep the two compositions from intermixing. A suitable example of a package for the present two-step mascara product is described in U.S. Pat. No. 7,473,045 to Dumler.

Figures 3A, 3B:
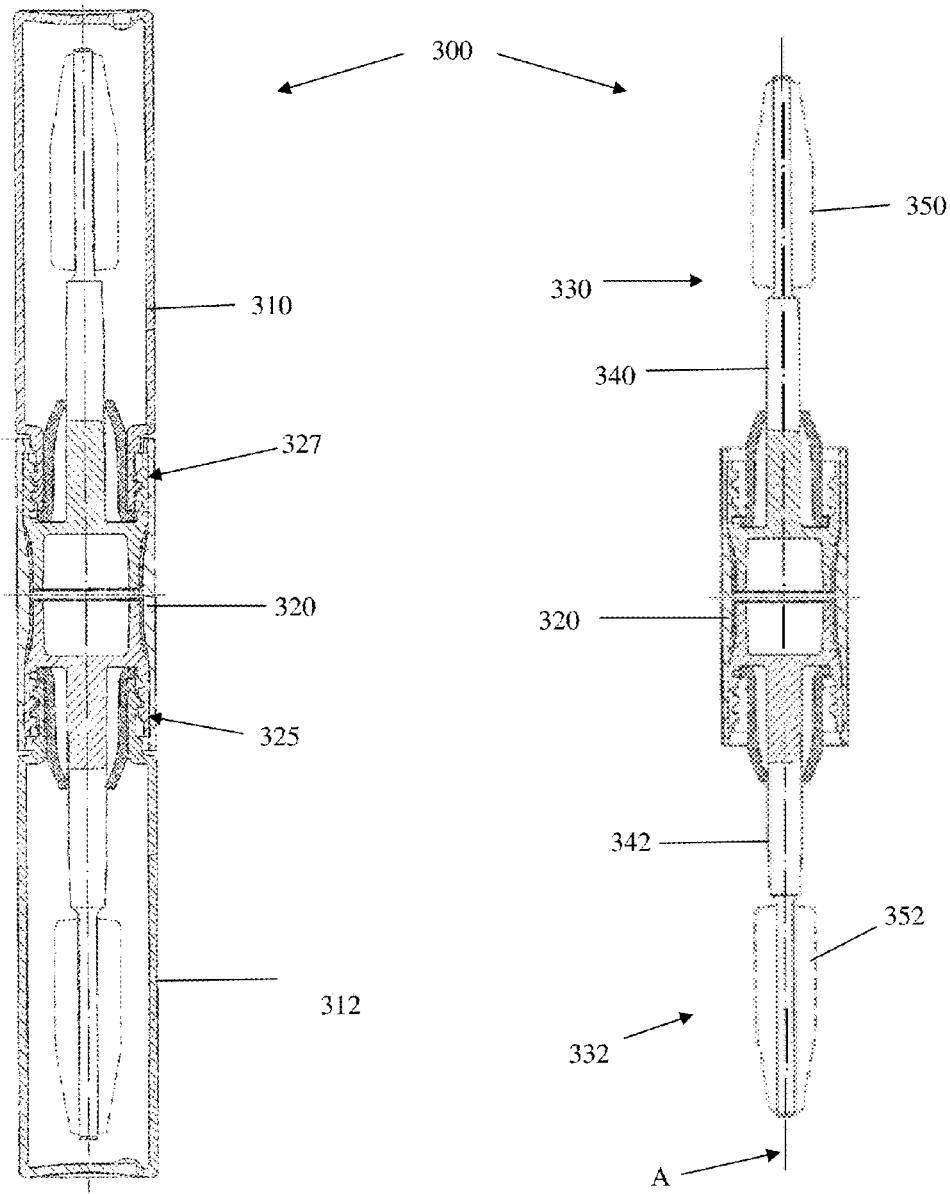
FIG. 3A is a plan view of a double-ended applicator.
FIG. 3B is a plan view of a double-ended applicator.

FIGS. 3A and 3B illustrate an exemplary duel-ended package 300 suitable for use herein. The package 300 shown in FIG. 3A includes two containers 310 and 312 suitable for storing and dispensing a mascara product disposed on opposing ends of a central ferrule 320. The containers 310 and 312 are each threadably joined to the central ferrule 320 by a set of threads 325 and 327. Of course, it is to be appreciated that the containers 310 and 312 may be joined to the ferrule 320 by any suitable means known in the art (e.g., snap fittings, twist-lock fittings and the like). FIG. 3B shows the package 300 with the containers 310 and 312 removed. Joined to the ferrule 320 and extending outwardly therefrom along a longitudinal axis A are two opposing applicators 330, 332. Each applicator 330, 332 includes an applicator head 340, 342 and an applicator stem 350, 352 that joins the head 340, 342 to the ferrule 320. One of the applicators 330 may be a twisted wire brush and the other applicator 332 may be a molded plastic brush, for example, as described therein. The applicators 330, 332, when not in use, may be covered by the containers 310, 312, as shown in FIG. 3A. During typical use of the two-step mascara product, only one of the applicators 330, 332 will be exposed at a time (i.e., have its associated container 310, 312 removed). Thus, the other container 310, 312, which is still joined to the central ferrule 320, may function as a suitable handle.

TEST METHODS

Rub Test
Equipment:
Smooth substrate for supporting the film for testing (e.g., 10"×5½" Leneta Form 2A Opacity Chart)
0.006" draw down bar
Draw down board (i.e., hard, flat surface suitable for supporting the Leneta chart and ample). White paper towel (or similar substrate) with sufficient strength to withstand test (e.g., WypAll L40 brand paper towels available from the Kimberly-Clark Corporation)
2½" diameter 2 kg weight
2½" diameter arch punch
Scissors
50° C. Oven
Double sided tape
Spectrophotometer (e.g., Datacolor Microflash 200d)

Procedure:
1. Drawdown Preparation:
   a. Place a Leneta card on a drawdown board, Black/White side up. Label the top right of the card with sufficient sample & solvent identification. Take care to touch the card as little as possible since skin oils can affect the film thickness of product on the card.
   b. Apply 1-2 ml of product in a line across the top of the card, and use a 0.006" drawdown bar to draw a film down the entire length of the card.
   c. Repeat steps 1a & 1b for all products to be tested.
   d. Once all draw downs have been completed, place them in a 50° C. oven for two hours. Take care not to mar the film surfaces.
   e. After an hour, remove the samples from the oven and allow them to equilibrate to ambient room temperature.
2. Sample Abrasion:
   a. Use an arch punch to punch out 2.5" diameter "abrasion substrate" disks from "WypAll" paper towels.
   b. Completely and evenly, (do not overlap) apply strips of double sided tape to the bottom of a 2 kg weight. Cut away excess tape that extends beyond the perimeter of the weight bottom. Place and adhere a single WypAll disk (1 ply thickness) to the sticky bottom of the weight. This will be used to abrade the film and see how much of it is removed.
   c. Place the disk/weight in the center of the first 3"×3" testing area. Twist the disk through two full revolutions in ⅛ revolution increments. Carefully remove the weight (up and away from the drawdown), and remove the abrading disk from the bottom of the weight. (Only change the double sided tape when a disk will no longer firmly adhere to the bottom of the weight.)
   d. Perform steps 3a, 3b, & 3c for all subsequent Leneta card drawdowns.
3. Color Measurement.
   The procedure below is described by using a Datacolor Microflash 200d brand spectrophotometer, but one of ordinary skill in the art will appreciate that other spectrophotometer capable of measuring a Delta L value on the L*C*h color scale may be equally suitable.
   a. Turn on the spectrophotometer.
   b. Press the 'Menu' key on the front of the spectrophotometer until the word "Set-up" appears.
   c. Click the button directly below the word "set-up" to select the set-up menu.
   d. Use the arrow keys to pick the calibration program.
   e. Set the 'hand-held head' to Specular Included. (Using the toggles on the head, confirm that "white" (vs black) is showing through port.)
   f. The calibration program prompts you to place the white tile under the spectrophotometer head and press the trigger.
   g. The prompt that instructs you to measure the Black Trap. Place the black trap under the head and squeeze the trigger.
   h. The calibration is now complete.
   i. Using the toggles on the back of the spectrophotometer's hand-held head, set the Specular to "Excluded". (Confirm that "black" is showing through the port.)
   j. Select 'Illuminant' from the Main Menu. Use the D65/10 setting.
   k. Select Display from the main menu. Select CIE LCH Data and choose add.
   l. To take measurements, press the large Menu Key on the front of the spectrophotometer.
   m. Select 'STD' from the menu. Select 'Temporary Standard'. Place the spectrophotometer over an unused abrasive disc over the white section of an unused Leneta card and take a reading by squeezing the trigger. This measurement is now set as the standard.
   n. Place a abrasive disc that has abraded a product film over the white section of an unused Leneta card then place the spectrophotometer over the disk and take a reading by squeezing the trigger.
   o. Record the Delta L value. Take 2 additional measurements of the sample, measuring a different area of the disk each time. The reported result for the test is the absolute value of the average of the 3 measurements.

EXAMPLE 1

A top coat as described herein may be made according to the method given directly below Table 1A using the ingredients and amount disclosed in Table 1A. The exemplary compositions in Table 1A are identified as prototypes 006, 017, 036 and 089.

TABLE 1A

Top Coat Compositions

| Phase | Material | Supplier/Trade Name | Function | 006 Wt % | 017 Wt % | 036 Wt % | 089 Wt % |
|---|---|---|---|---|---|---|---|
| A | Tall Oil Glycerides | Arizona Chemical Sylvagum RE 85K | Film Former | 12.5 | 8.5 | 12.5 | 12.5 |
| A | Pentaerythrityl Hydrogenated Rosinate | Eastman Foral 105-E | Film Former | 12.5 | 8.5 | 12.5 | 12.5 |
| A | 1,2 Hexanediol and Caprylyl Glycol | Symrise Symdiol 68 | Preservative | 1 | 1 | 1 | 1 |
| A | Isododecane | Presperse Permthyl 99A | Volatile Solvent | 45.88 | 53.88 | 50.50 | 45.88 |
| B | Disteardimonium Hectorite | Elementis Bentone 38V CG | Structurant | 14 | 14 | 14 | 14 |

TABLE 1A-continued

Top Coat Compositions

| Phase | Material | Supplier/Trade Name | Function | 006 Wt % | 017 Wt % | 036 Wt % | 089 Wt % |
|---|---|---|---|---|---|---|---|
| C | Propylene Carbonate | Huntsman Jeffsol | Polar Activator | 4.62 | 4.62 | — | 4.62 |
| D | Black Iron Oxide (Jet Milled) | Sensient Unipure Black LC 989 EM | Colorant | 9.5 | 9.5 | 9.5 | — |
| D | Triethoxycaprylsilane coated Black Iron Oxide (Jet Milled) | Sensient Unipure Black LC 989 EM AS | Colorant | — | — | — | 9.5 |
| | TOTAL | | | 100.000 | 100.000 | 100.000 | 100.00 |

Phase A ingredients are melted and mixed together with low shear mixing.
Phase B is gradually added to the Phase A and then dispersed with high shear mixing.
Phase C is then added and mixed in with high shear mixing.
Phase D is then added and dispersed with high shear mixing. The batch is cooled to ambient conditions.

EXAMPLE 2

Table 1B lists another example of a top coat composition. The composition is made according to the procedure immediately following Table 1B.

TABLE 1B

| Phase | Material | Wt % |
|---|---|---|
| A | Isododecane | 45.5 |
| A | 1,2 Hexanediol and Caprylyl Glycol | 1 |
| A | Benzyl Alcohol | 0.65 |
| B | Tall Oil Glycerides | 13.5 |
| B | Pentaerythrityl Hydrogenated Rosinate | 13.5 |
| C | Black Iron Oxide (Jet Milled) | 10 |
| D | Disteardimonium Hectorite | QS |

Procedure: Phase A ingredients are melted and mixed together with low shear mixing. Phase B is gradually added to the Phase A and then dispersed with high shear mixing. Phase C is then added and dispersed with high shear mixing. Phase D is added and the batch is cooled to ambient conditions.

In order to demonstrate the improved wear resistance of the present top coat as compared to conventional mascara composition that use rosin esters, both mascara composition were subject to the Rub Test. The comparative mascara compositions are set forth in Table 2A, and were prepared according to the process immediately following Table 2A.

TABLE 2A

Comparative Mascara Compositions

| No. | Component | Trade Name | Ex 1 % W | Ex 2 % W | Ex 9 % W |
|---|---|---|---|---|---|
| 1 | Hydrogenated ester gum | Pine crystal KE-311 | 8 | 15 | 8 |
| 2 | Hydrogenated Pentaerythrityl Rosinate | Ester gum HP | 8 | 10 | 8 |
| 3 | Carnauba Wax | | 3 | 3 | 3 |
| 4 | Beeswax | | 5 | 5 | 5 |
| 5 | Dextrin fatty acid ester | Rheopearl TL | 3 | 3 | — |
| 6 | Organic modified bentonite | | 2 | 2 | 2 |
| 7 | Silicone-treated black iron oxide | 5% dimethicone treatment | 8 | 8 | 8 |
| 8 | Talc | | 5 | 5 | 5 |
| 9 | Sericite | | 2 | 2 | 2 |
| 10 | Silicic anhydride | Aerosil 200 | 2 | 2 | 2 |
| 11 | Light liquid isoparaffin | IP Sorbent 1620MU | qs | qs | qs |
| | TOTAL | | 100 | 100 | 100 |

Examples 1, 2, and 9 of JP 2009-114099 were prepared as follows:
A. Components 1-3 were heated to about 110° C. and mixed to homogeneity.
B. Components 4-11 were added to A and mixed to homogeneity.
C. The composition of step B was placed in containers to obtain oil-based mascaras.

The results of the Rub Test are illustrated in Table 2B. As can be seen in Table 2B, the present top coat compositions exhibit a suitable Average Delta L value of less than 2.5, while the comparative compositions do not. Other suitable Delta L values are less 2.0 or less than 1.5.

TABLE 2B

Rub Test Results

| | Avg Delta L |
|---|---|
| Inventive Mascara Compositions | |
| Prototype 006 | −0.20 |
| Prototype 017 | −0.88 |
| Prototype 036 | −1.65 |
| Prototype 089 | −0.67 |

TABLE 2B-continued

Rub Test Results

| Comparative Compositions | Avg Delta L |
|---|---|
| JP 2009-114099 Mascara Example # 1 | −3.56 |
| JP 2009-114099 Mascara Example # 2 | −4.70 |
| JP 2009-114099 Mascara Example # 9 | −4.27 |

Scanning Electron Microscopy

Scanning electron microscopy (SEM) is used to compare the morphologies of mascara films applied to false lashes. A set of Ardell® 109 brand false eyelashes are trimmed to a length of approximately 0.95 cm and affixed to a metal bar. Five strokes of mascara are applied to a false eyelash sample using an automated mascara applicator device. The samples are allowed to dry completely. Individual lashes are removed from the metal bar and adhered to an SEM sample stub with carbon tape. The edges of the lashes are secured with silver paint. Samples are frozen in liquid nitrogen and then transferred to the Alto 2500 sample chamber to defrost at −95 C for 10 minutes. Samples are lightly coated with platinum before observation. Samples are observed using a Hitachi S4700 field emission SEM equipped with a Gatan Alto 2500 cryo stage and representative images are collected at −105 C in the cryo-SEM under the following conditions: kV=15 kV, $I_e$=10 μA, Mode=ultra high resolution, Detector=Mixed, Working Distance=~15 mm.

Figure 4:
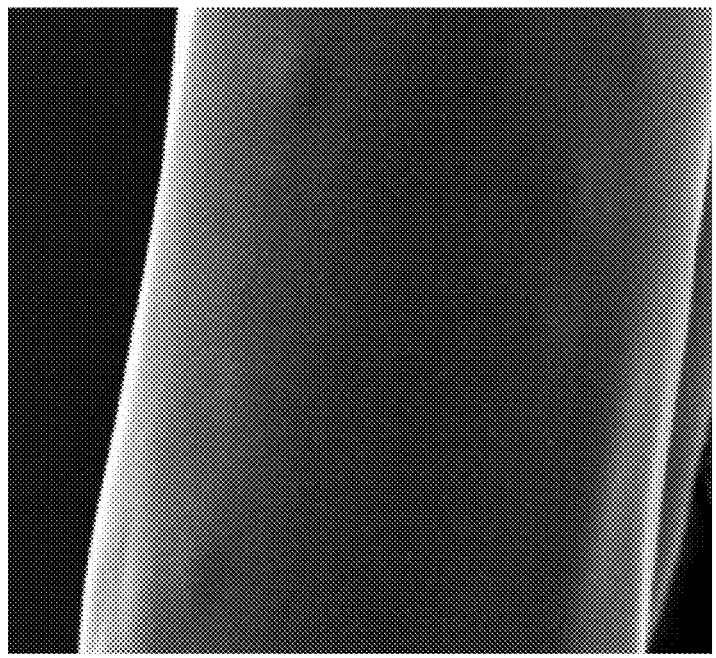
FIGS. 4-12 are scanning electron micrographs of films formed from a variety of mascara combinations applied in a two-step process to an artificial eyelash.
Figure 5:
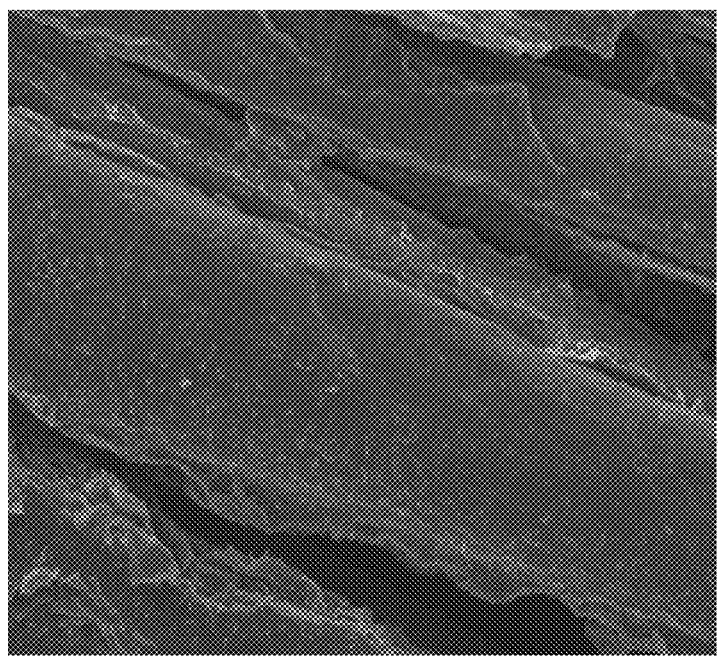
Figure 6:
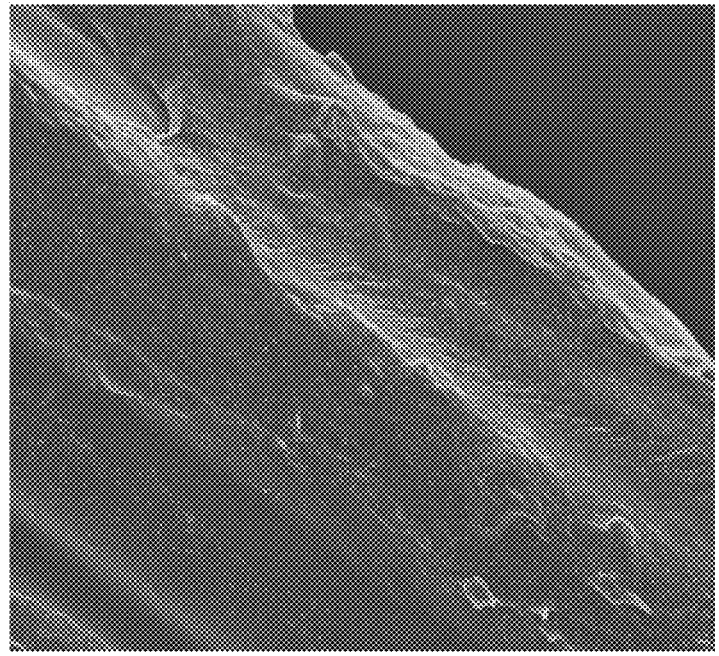
Figure 7:
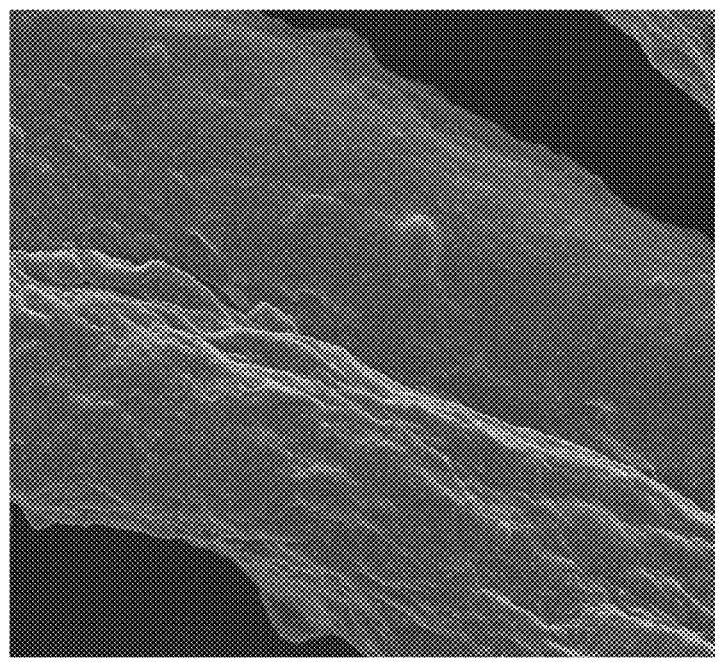
Figure 8:
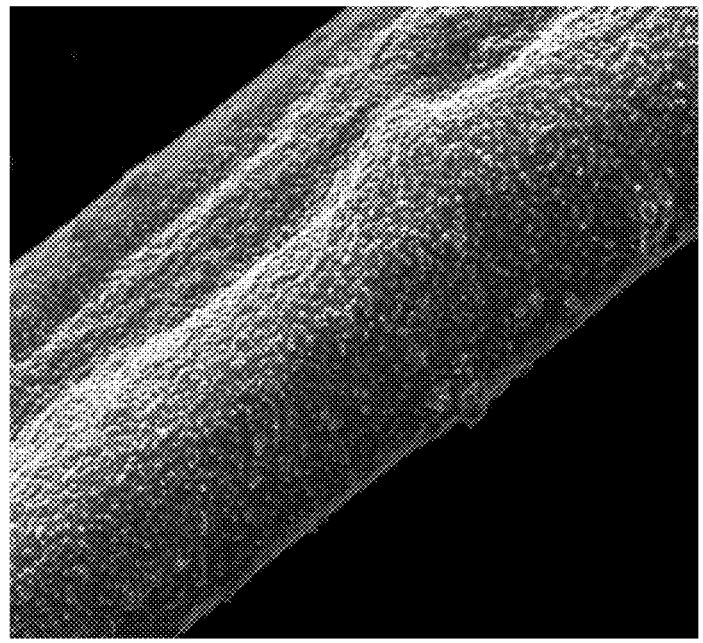
Figure 9:
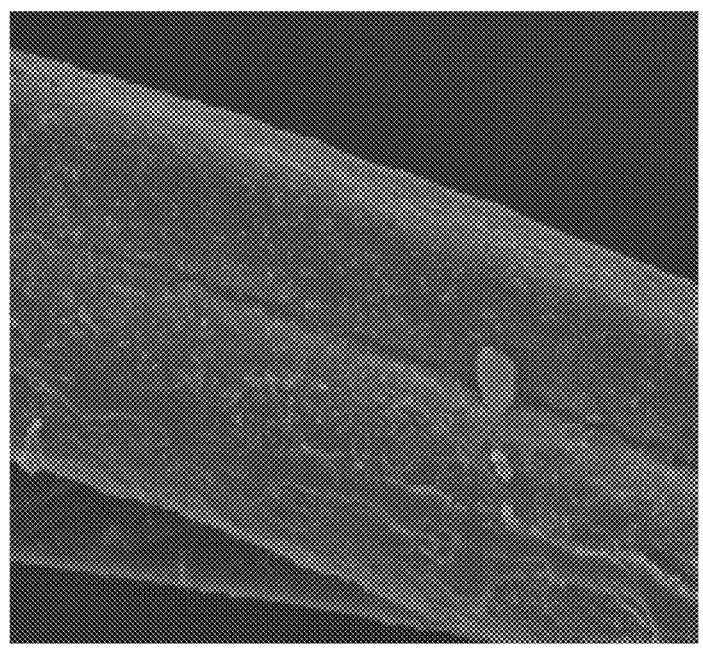
Figure 10:
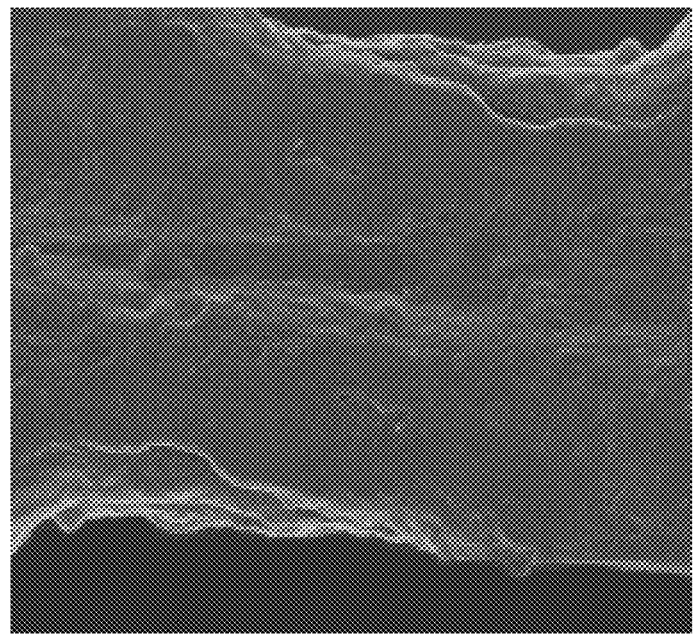
Figure 11:
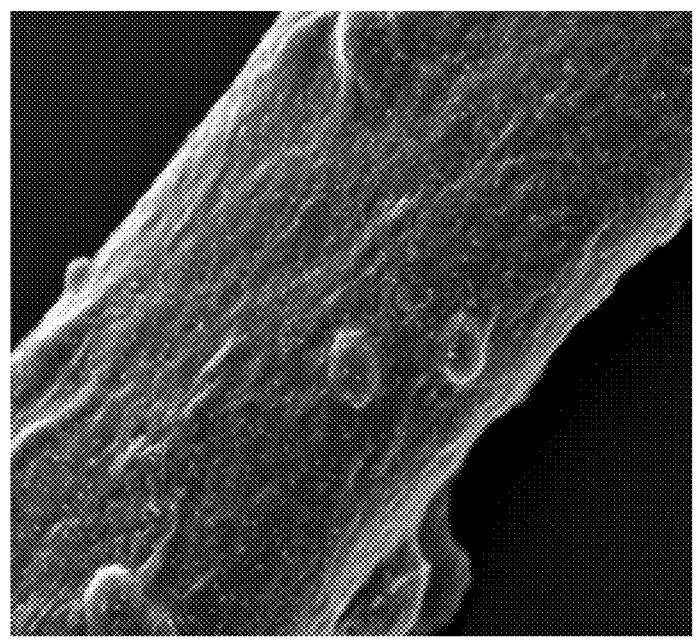
Figure 12:
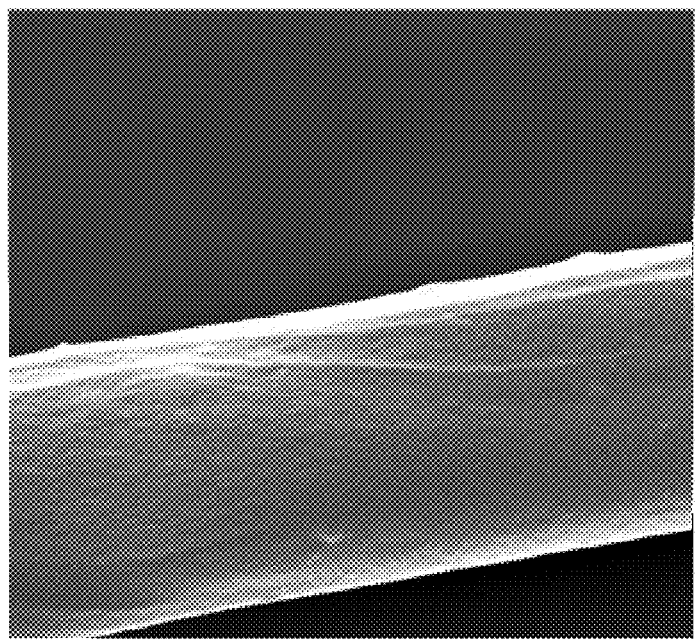
Figure 13:
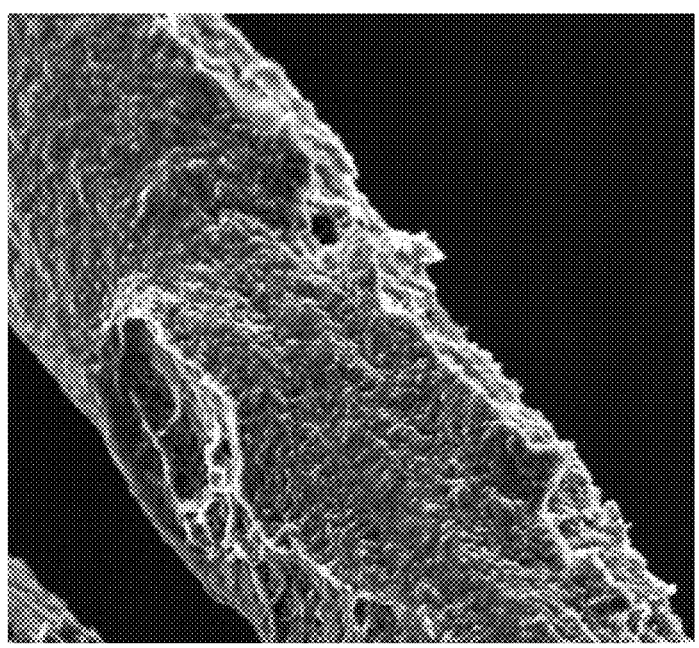
FIGS. 13-22 are scanning electron micrographs of films formed from the same base coat and top coat applied in a two-step process to an artificial eyelash using a variety of different mascara applicator combinations.
Figure 14:
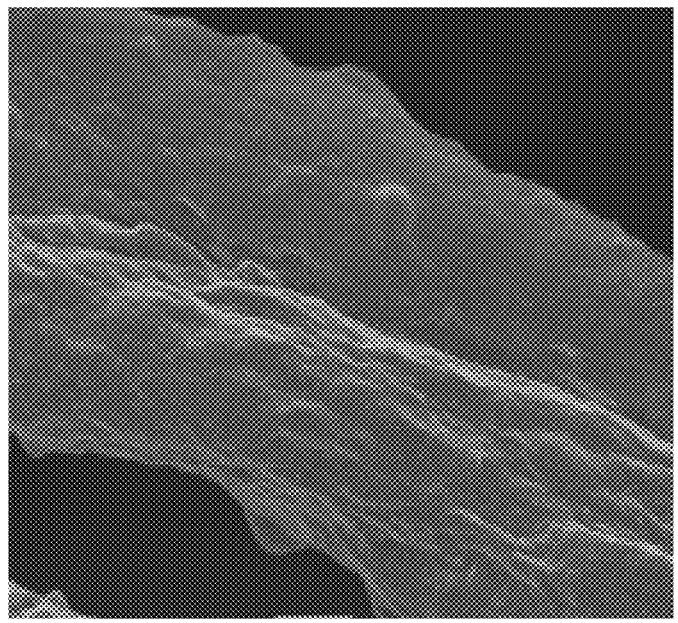
Figure 15:
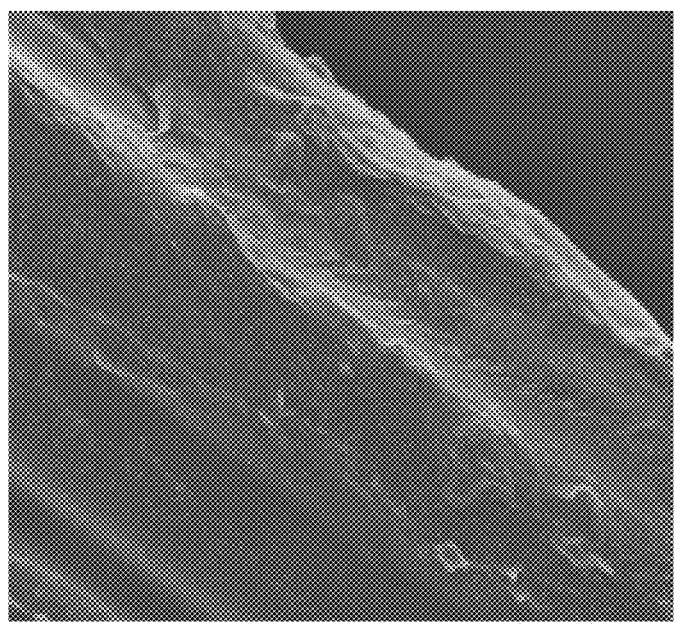
Figure 16:
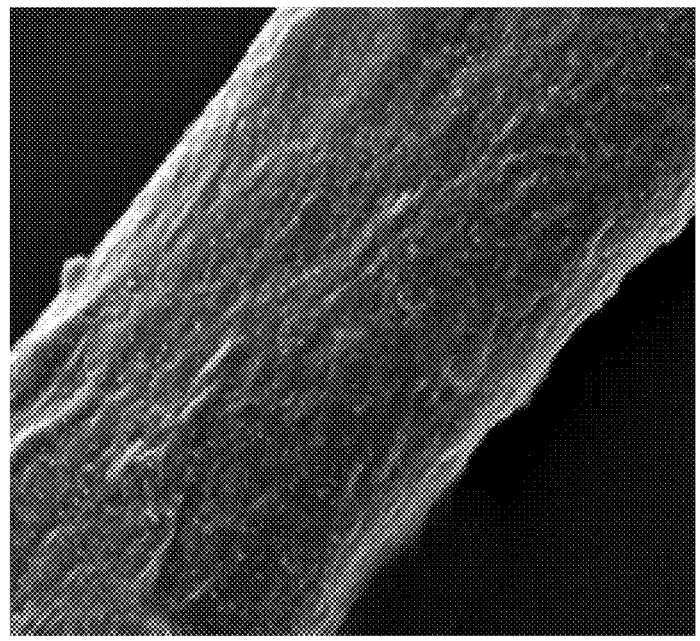
Figure 17:
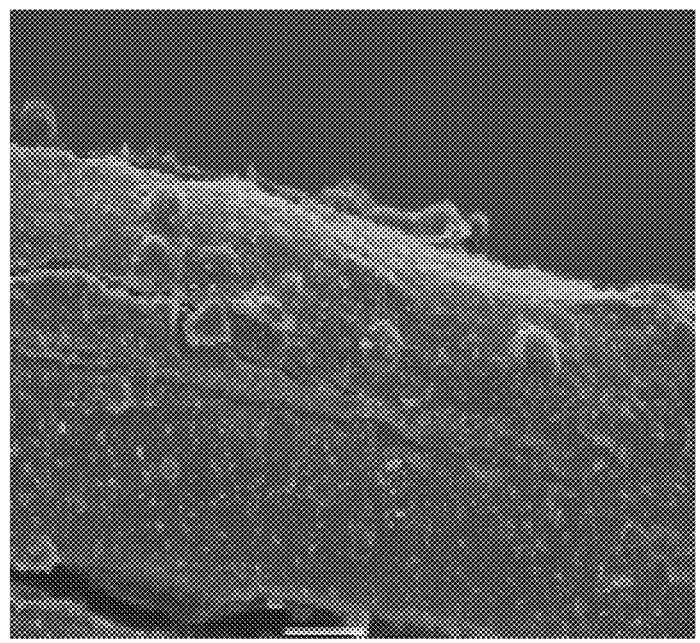
Figure 18:
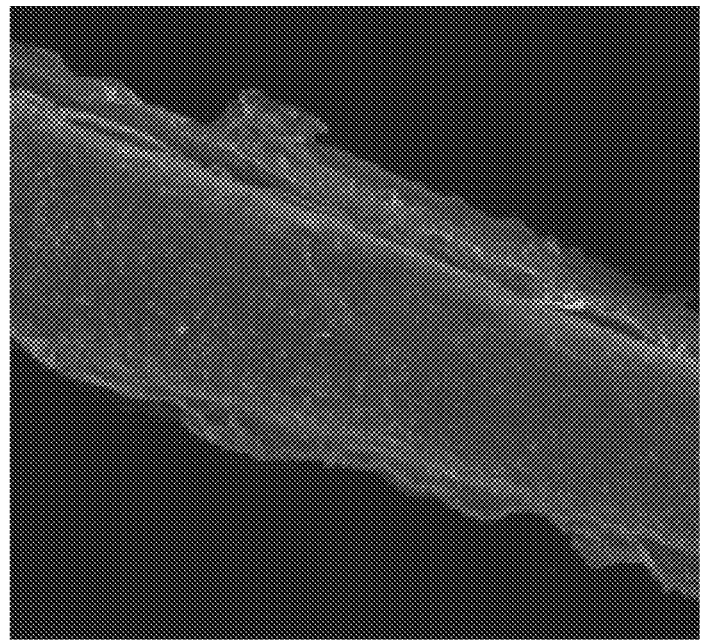
Figure 19:
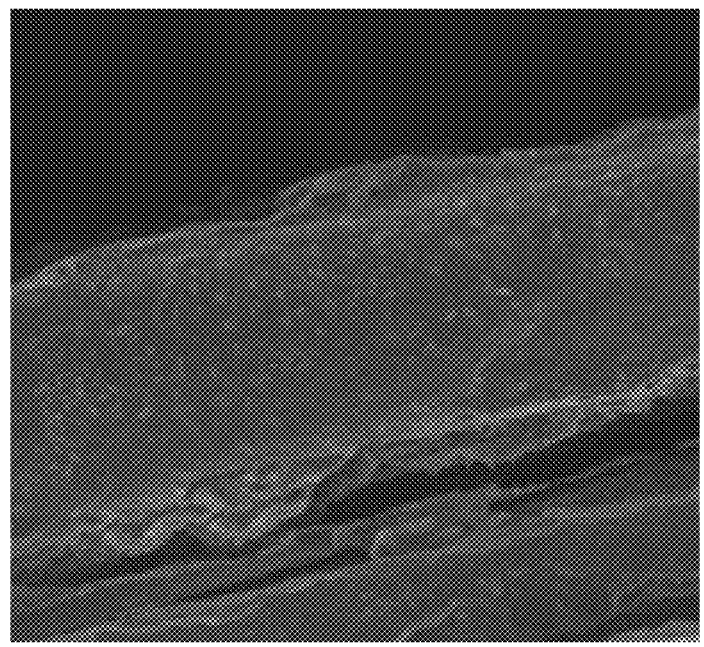
Figure 20:
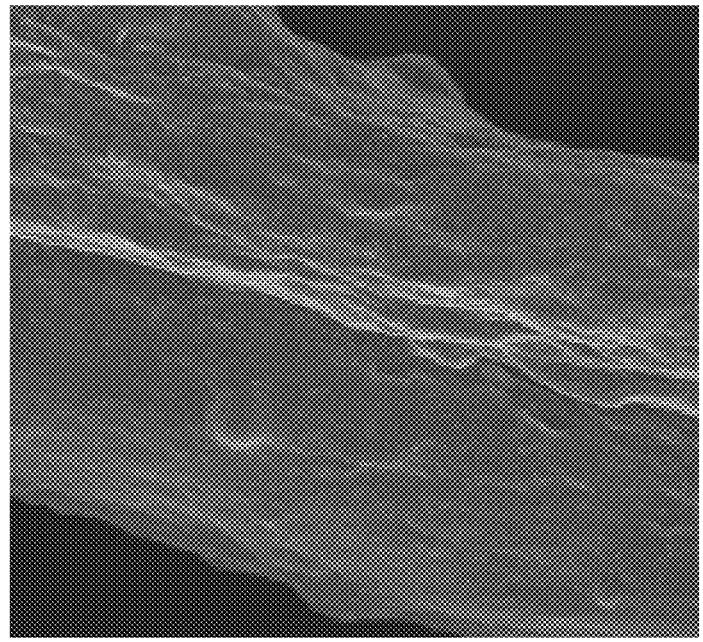
Figure 21:
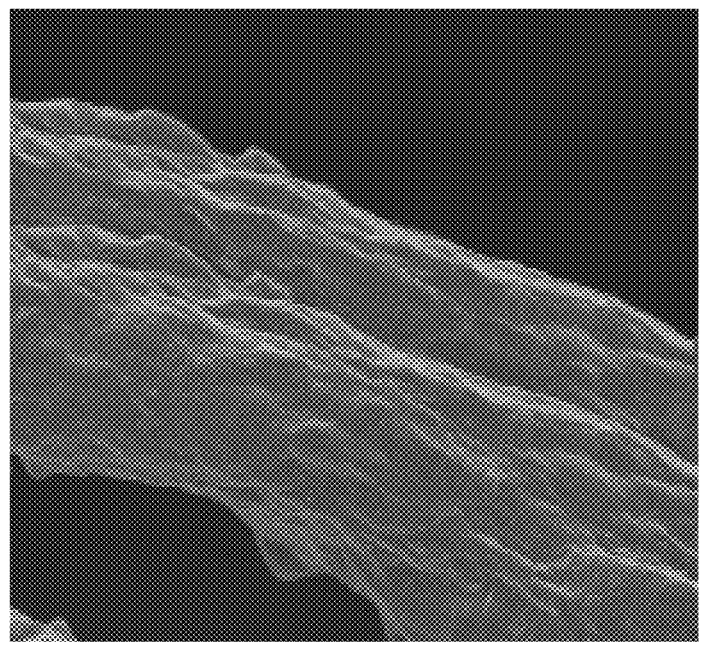
Figure 22:
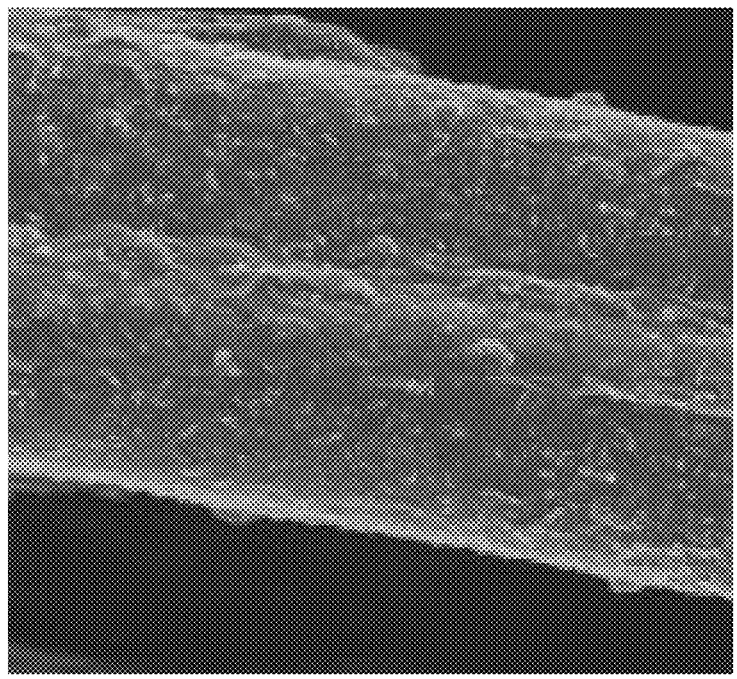

Cryo-SEM was performed on films formed from a variety of combinations of mascara compositions applied in a two-step process. Table 3 lists the mascara combinations used and FIGS. 4-12 show the resultant micrographs at 300× magnification. All of the base coat compositions in Table 3 were applied with a large molded plastic brush, and all the top coat compositions were applied with a small twisted wire brush. The top coat was applied immediately after the base coat was applied. The CoverGirl Volum' Express® brand mascara is an exemplary base coat composition as described herein. The Max Factor False Lash Effect®Waterproof brand mascara ("FLE") available from the Procter & Gamble Company is a, lower viscosity, lower wax content mascara composition that appears "shiny" and "jetty" in color when applied alone. The FLE mascara was chosen as a comparative example to show that a viscosity difference and lack of waxes does not necessarily provide the volumizing benefit and smooth, continuous film of the present two-step mascara product. The top coat used was prototype 036 from Table 1A. As can be seen in Table 3 and FIGS. 4-12, only the combination of the present base coat applied with a molded plastic brush and the present top coat applied with the small twisted wire brush, as illustrated in FIG. 4, provided a suitable smooth, continuous film.

TABLE 3

| Base coat | Top coat | Figure |
|---|---|---|
| CoverGirl Volum' Express ® | Prototype 036 | 4 |
| Prototype 036 | CoverGirl Volum' Express ® | 5 |
| CoverGirl Volum' Express ® | FLE | 6 |
| FLE | CoverGirl Volum' Express ® | 7 |
| FLE | Prototype 036 | 8 |
| Prototype 036 | FLE | 9 |
| FLE | FLE | 10 |
| CoverGirl Volum' Express ® | CoverGirl Volum' Express ® | 11 |
| Prototype 036 | Prototype 036 | 12 |

Cryo-SEM was also performed on films formed from the present two-step mascara product applied with a variety of mascara applicator types (i.e., small and large molded plastic brushes and small and large twisted wire brushes). The base coat composition is CoverGirl Volum' Express® brand mascara and the top coat composition is prototype 036 from Table 1A. Table 4 lists the applicator combinations used and FIGS. 13-22 show the resultant micrographs at 300× magnification. As can be seen in FIGS. 13-22, only the combination of the present base coat applied with the large molded plastic brush and the top coat applied with the small twisted wire brush, as illustrated in FIG. 4, provided a suitable smooth and continuous film.

TABLE 4

| Base coat brush | Top coat brush | Figure |
|---|---|---|
| Small Twisted wire | Large Twisted wire | 13 |
| Large Twisted wire | Large Moltrusion | 14 |
| Small moltrusion | Large Moltrusion | 15 |
| Small Twisted wire | Small Twisted wire | 16 |
| Large moltrusion | Large moltrusion | 17 |
| Small moltrusion | Small moltrusion | 18 |
| Small moltrusion | Large moltrusion | 19 |
| Large moltrusion | Small moltrusion | 20 |
| Small moltrusion | Large Twisted wire | 21 |
| Small Twisted wire | Small moltrusion | 22 |

To demonstrate the superior color cosmetic benefits of the present two-step mascara product, a variety of mascara composition and applicator combination were screened through a sequential monadic test against the present two-step mascara product. Thirty female test subjects used a randomized order of product combinations as set forth in Table 5 below. For each test, the test subjects were asked to apply the base coat and top according to their usual mascara application habit, without waiting for the base coat to dry before applying the top coat. It is believed that the immediate application of the top coat is more representative of how consumers actually use two-step mascara products, and provides a most robust test to demonstrate superior product performance.

Once applied, the test subjects were asked to grade the mascara performance on a 5 point scale ranging from the strongly agree to strongly disagree (strongly agree, agree, neither agree nor disagree, disagree, and strongly disagree) describing the volume and the intensity of the look against the following 3 statements:

1) This mascara gave my lashes extra-ordinary volume.
2) This mascara gave my lashes intensely dark volume.
3) This mascara gave me smooth looking volume.

After answering these questions, the test subjects were instructed to remove the mascara, let their lashes dry for 10 minutes, and repeat the above process with the second mascara. After completing of this second questionnaire, which included the above three statements, the test subjects were asked to indicate which of the products they preferred.

Table 5 illustrates the tested combinations and the results of the test. The data shown are the percentage of test subjects who responded to the statement with an answer of either "strongly agree" or "agree." The data also show how many of the test subjects preferred the present two-step mascara product to the comparative product. In Tests 1-3, a large molded plastic brush was used to apply the base coat shown in Table 5, and a small twisted wire brush was used to apply the top coat shown in Table 5. In Tests 4-6, CoverGirl Volum' Express® was used as the base coat and prototype 036 was used as the top coat, and each composition was applied with the brush indicated in Table 5.

Test 1 compares the present two-step product to a product that used the same compositions but applied in reverse order (i.e., the top coat was applied first followed by the base coat). As can be seen in Table 5, the present two-step mascara composition provided superior volume and color benefit and was preferred over the comparative product by 29 out of 30 test subjects. Test 2 compared the novel two-step product to a combination of CoverGirl Volum' Express® and FLE. Similarly, in Test 2 and 3, the present two-step product provided superior color and volume benefit over the comparative products and was preferred by a vast majority of the test subjects. Tests 4-6 illustrate the importance of applicator selection. As can be seen in Table 5, the base coat and top coat of the present two-step product, when applied with a large molded plastic brush and a small twisted wire brush, respectively, provide a superior volume benefit and color intensity relative to the other brush combinations tested.

TABLE 5

| Test | Base Coat | Top Coat | Extraordinary volume | Intensely black | Smooth volume | Preferred by |
|------|-----------|----------|----------------------|-----------------|---------------|--------------|
| 1 | CoverGirl Volum' Express ® | Prototype 036 | 90 | 97 | 97 | 29/30 |
|   | Prototype 036 | CoverGirl Volum' Express ® | 40 | 40 | 40 | 1/30 |
| 2 | CoverGirl Volum' Express ® | Prototype 036 | 97 | 93 | 97 | 28/30 |
|   | CoverGirl Volum' Express ® | FLE | 33 | 37 | 33 | 2/30 |
| 3 | CoverGirl Volum' Express ® | Prototype 036 | 93 | 93 | 97 | 30/30 |
|   | CoverGirl Volum' Express ® | CoverGirl Volum' Express ® | 37 | 37 | 40 | 0/30 |
| 4 | Large molded plastic brush | Small twisted wire brush | 97 | 97 | 97 | 27/30 |
|   | Small twisted wire brush | Large molded plastic brush | 33 | 37 | 33 | 3/30 |
| 5 | Large molded plastic brush | Small twisted wire brush | 97 | 93 | 93 | 27/30 |
|   | Large twisted wire brush | Small twisted wire brush | 40 | 40 | 40 | 3/30 |
| 6 | Large molded plastic brush | Small twisted wire brush | 93 | 93 | 97 | 28/30 |
|   | Large molded plastic brush | Small molded plastic brush | 33 | 37 | 37 | 2/30 |

Figure 23A:
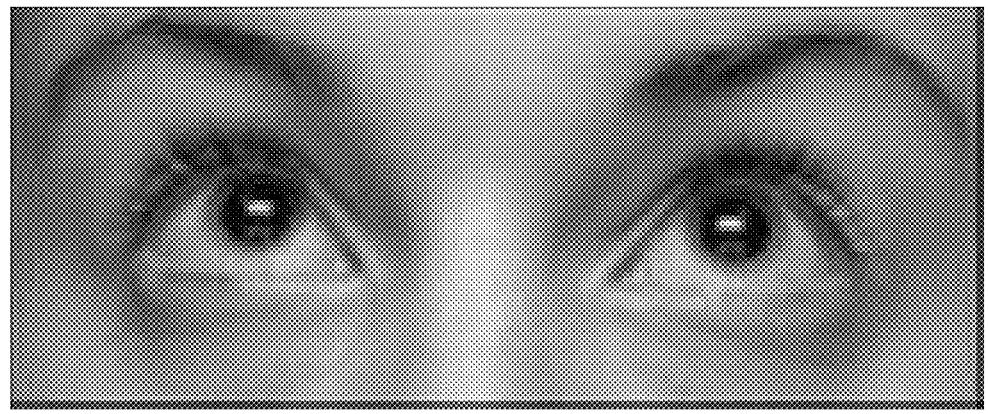
FIG. 23A shows an image of eyelashes captured prior to applying a mascara product.
Figure 23B:
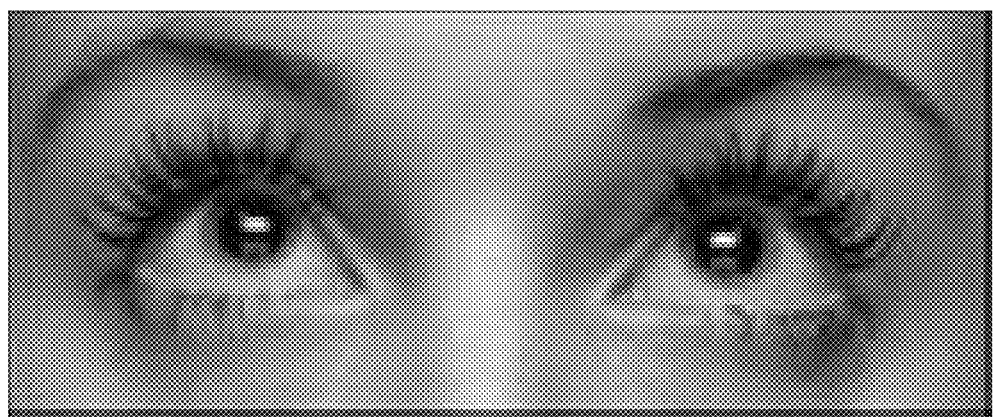
FIG. 23B shows an image of eyelashes captured after applying the present two-step mascara product.

Table 6 illustrates the long-wear characteristics of the present two-step mascara product. CoverGirl Volum' Express® was selected for use as an exemplary base coat and prototype 036 was selected for use as an exemplary top coat. A large molded plastic brush was used to apply the base coat and a small twisted wire brush was used to apply the top coat. Forty female test subjects were asked to apply only the base coat to the eyelashes of one eye in the manner they normally used to apply mascara. The same test subjects were also asked to apply the base coat followed by the top coat to the eyelashes of their other eye in the manner they normally use to apply mascara. Prior to applying any mascara, the eyelashes of both eyes of the test subjects were analyzed to determine a base line volume. The eyelash analysis involved capturing an image of the eyelashes with a high resolution camera (i.e., greater than 10 Megapixel) with flash and measuring the thickness of the eyelashes at the midpoint of the shaft with image analysis software (e.g., Optimas® 6.5 software). The eyelashes of the test subjects were analyzed again immediately after application of the mascara products to determine the initial change in volume. The eyelashes of the test subject were analyzed again twenty-four hours after application of the mascara products to determine the change in volume. FIG. 23A shows an image of eyelashes captured prior to applying a mascara product. FIG. 23B shows an image of eyelashes captured after applying the present two-step mascara product.

The data shown in Table 6 illustrate the change in volume of the eyelashes relative to the initial baseline volume averaged across all of the test subjects. As can be seen in Table 6, the base and top coat combination of the present two-step mascara product not only provides superior initial volume benefit but also provides the superior volume benefit for more than 24 hours.

TABLE 6

|  | Base coat only | Base and top coat |
|---|---|---|
| % increase after application | 241 | 290 |
| % increase after 24 hours | 180 | 280 |

Table 7 illustrates the long-wear characteristics of the present two-step mascara product based on consumer perception. The same test subjects from the long-wear test described above were asked to grade the mascara performance on a 5 point scale (strongly agree, agree, neither agree nor disagree, disagree, and strongly disagree) describing the volume of the look against the following 3 statements:

1) This mascara volumizes my lashes.
2) This mascara creates intensely dark volume.
3) This mascara creates volume that lasts for 24 hours.

The data in Table 7 indicate the percentage of test subjects who responded who responded to the statement with an answer of either "strongly agree" or "agree." As can be seen in Table 7, the test subjects not only perceived that the present two-step mascara product provided superior volume and color intensity benefits, but overwhelmingly perceived that the present two-step product provided these benefits for 24 hours.

TABLE 7

|  | Volumizes my lashes | Creates intensely dark volume | Volume lasts for 24 hours |
|---|---|---|---|
| Base Coat Only | 88 | 83 | 45 |
| Base Coat and Top Coat | 93 | 93 | 95 |

Table 8 illustrates the synergistic color benefit as perceived by a consumer. Twenty test subjects were asked to apply each of the mascara compositions listed in Table 8. Once applied, the test subjects were asked to grade the mascara performance on the 5 point scale described above describing the intensity of the look against the following statement: this mascara gave my lashes intensely dark volume. After answering the questionnaire, the test subjects removed the mascara composition prior to apply the next composition. The data shown in Table 8 are percentages of test subjects who responded to the statement with either "strongly agree" or "agree." The base coat used was CoverGirl Volum' Express and the top coat was prototype 036. For the two-step product, the top coat was applied immediately after the base coat. As can be seen in Table 8, the test subjects perceived the present two-step product as providing a more intense, dark volume look than either of the individual compositions.

TABLE 8

| Mascara | This mascara gave my lashes intensely dark volume |
|---|---|
| Two-step product | 95 |
| Base coat | 70 |
| Top coat | 45 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A two-step mascara product comprising:
   a. a first mascara composition, the first mascara composition including a film-forming polymer comprising an organosiloxane and a plurality of primary particles having an effective diameter of at least 5 microns dispersed in a first carrier, the first mascara composition having a viscosity in the range of 350,000 to 1,000,000 centipoise;
   b. a second mascara composition second mascara composition comprising from 7% to 10% by weight of jet milled iron-oxide, said second mascara composition having a Critical Pigment Volume Concentration. the second mascara composition including from 10-80% by weight of a volatile second carrier consisting of isododecane and from 15-35% by weight of a film-former comprising a mixture of tall oil glyceride and at least one of pentaerythrityl rosinate or hydrogenate thereof, the second mascara composition having a viscosity in the range of 150,000 to 300,000 centipoise and a Delta L value of less than 2.5 according to the Rub Test; and wherein said film-former comprises equal amounts of said tall oil glyceride and said rosinate, wherein said glyceride and said rosinate are each present at concentrations in the range of 8.5% to 13.5% of weight of the composition;
   c. distearyl dimonium hectorite clay particles as a thickener at a concentration of 10%-15% by weight of the second mascara composition; and
   d, wherein the solids volume concentration of said second mascara composition, based on the volume concentration of said iron oxide particles and said clay particles, is less than the Critical Pigment Volume Concentration;
   e. a double-ended package for storing and dispensing each of the first and second mascara compositions, the package comprising a molded plastic applicator joined to one end of a central ferrule and a twisted wire applicator joined to the opposing end of the central ferrule, the double-ended package further comprising a first container that is threadably engeagable with the central ferrule such that when it is engaged thereto the first container covers the molded plastic applicator, and a second container that is threadably engageable with the central ferrule such that when it is engaged thereto the second container covers the twisted wire applicator; wherein said molded plastic applicator is adapted to apply said first mascara composition as a base coat and said wire applicator is adapted to apply said second mascara composition as a top coat.

* * * * *